United States Patent
Mikolajczyk et al.

(10) Patent No.: US 7,659,073 B2
(45) Date of Patent: Feb. 9, 2010

(54) FORMS OF PROSTATE SPECIFIC ANTIGENS AND METHODS FOR THEIR DETECTION

(75) Inventors: Stephen D. Mikolajczyk, San Diego, CA (US); Harry G. Rittenhouse, Del Mar, CA (US); Tang Jang Wang, Poway, CA (US); Robert L. Wolfert, Palo Alto, CA (US)

(73) Assignee: Hybritech Incorporated, San Diego, CA (US)

( * ) Notice: Subject to any disclaimer, the term of this patent is extended or adjusted under 35 U.S.C. 154(b) by 1800 days.

(21) Appl. No.: 09/792,534

(22) Filed: Feb. 23, 2001

(65) Prior Publication Data

US 2002/0045198 A1 Apr. 18, 2002

Related U.S. Application Data

(63) Continuation-in-part of application No. 09/302,965, filed on Apr. 30, 1999, now abandoned, which is a continuation-in-part of application No. 09/251,686, filed on Feb. 17, 1999, now abandoned, which is a continuation of application No. 08/846,408, filed on Apr. 30, 1997, now abandoned.

(51) Int. Cl.
*G01N 33/53* (2006.01)
(52) U.S. Cl. .................. 435/7.1; 530/300; 530/350
(58) Field of Classification Search .................. 435/7.1; 530/300, 350
See application file for complete search history.

(56) References Cited

U.S. PATENT DOCUMENTS 7,288,636 B2   10/2007   Mikolajczyk et al.

FOREIGN PATENT DOCUMENTS

| EP | 0 725 139 A2 | 8/1996 |
|----|--------------|--------|
| EP | 0 843 006 A2 | 5/1998 |
| WO | WO 94/10343 A1 | 5/1994 |
| WO | WO 96/34964 A2 | 11/1996 |
| WO | WO 98/49323 | 11/1998 |

OTHER PUBLICATIONS

Lin et al, 1998, Urology, 52: 366-371.*
Kibel, AS et al, 2000, J urol, 164(1): 192-6.*
Dong et al, 2000, Cancer Research, 60: 3880-3883.*
Zhau, HE, 1994, J Cell Biochem, Suppl 19: 208-216.*
W.J. Catalona, M.D., et al. Measurement of Prostate-Specific Antigen in Serum as a Screening Test for Prostate Cancer. N. Engl J Med, 324: 1156-1161, 1991.
J.E. Oesterling, Prostate Specific Antigen: A Critical Assessment of the Most Useful Tumor Marker for Adenocarcinoma of the Prostate. J Urol, 145: 907-923, 1991.
F. Labrie, et al., Serum Prostate Specific Antigen as Pre-screening Test for Prostate Cancer. J Urol, 147: 846-851, 1992.
H. Lilja, et al. Prostate-Specific Antigen in Serum Occurs Predominantly in Complex with $\alpha_1$-Antichymotrypsin. Clin Chem, 37: 1618-1625, 1991.
U.H. Stenman, et al. A Complex Between Prostate-specific Antigen and $\alpha_1$-Antichymotrypsin Is the Major Form of Prostate-specific Antigen in Serum of Patients with Prostatic Cancer: Assay of the Complex Improves Clinical Sensitivity for Cancer. Cancer Res., 51: 222-226, 1991.
W.J. Catalona, M.D., et al. Use of the Percentage of Free Prostate-specific Antigen to Enhance Differentiation of Prostate Cancer from Benign Prostatic Diease: A Prospective Multicenter Clinical Trial. Jama, 279: 1542-1547, 1998.
D. L. Woodrum, et al. Interpretation of Free Prostate Specific Antigen Clinical Research Studies for the Detection of Prostate Cancer. J Urol, 159: 5-12, 1998.
J. Peter, et al. Analysis of Free Prostate-specific Antigen (PSA) after Chemical Release from the Complex with $\alpha_1$-Antichymotrypsin (PSA-ACT). Clin. Chem 46: 474-482, 2000.
J. Noldus, et al. Isolation and Characterization of Free Form Prostate Specific Antigen (f-PSA) in Sera of Men With Prostate Cancer. J Urol., 158: 1606-1609, 1997.
H. Hilz, et al. Molecular Heterogeneity of Free PSA in Sera of Patients with Benign and Malignant Prostate Tumors [In Process Citation]. Eur Urol, 36: 286-292, 1999.
E. Paus, et al. Epitope Mapping and Affinity Estimation of 83 Antibodies against Prostate-Specific Antigen. Tumor. Biol., 20: 52-69, (*Suppl 1*)1999.
P. Nurmikko, et al. Production and Characterization of Novel Anti-Prostate-specific Antigen (PSA) Monoclonal Atibodies That Do Not Detect Internally Cleaved Lys145-Lys146 Inactive PSA [In Process Citation]. Clin.Chem., 46: 1610-1618, 2000.
T.J. Wang, et al. Western Blotting Analysis of Antibodies to Prostate-Specific antigen: Cross-Reactivity with Human Kallikrein-2. Tumor Biol, 20: 75-78 (Suppl. 1), 1997.
T.J. Wang, et al. Western Blotting Analysis of Antibodies to Prostate-Specific Antigen: Specificities for Prostate-Specific Antigen and Prostate-Specific Antigen Fragments. Tumor Biol., 20: 79-85 (suppl 1) 1999.
J. A. Finlay, et al. Polyclonal and Monoclonal Antibodies to Prostate-Specific Antigen Can Cross-React with Human Kallkrein 2 and Human Kallikrein 1. Urology, 53: 746-751, 1999.
A. Kumar, et al. Expression of Pro Form of Prostate-specific Antigen by Mammalian Cells and Its Conversion to Mature, Active Form by Human Kallikrein 2. Cancer Res, 57: 3111-3114, 1997.
A. Christensson, et al. Enzymatic Activity of Prostate-specific Antigen and Its Reactions with Extracellular Serine Proteinase Inhibitors. Eur J Biochem, 194: 755-763, 1990.

(Continued)

*Primary Examiner*—Larry R. Helms
*Assistant Examiner*—Minh-Tam Davis
(74) *Attorney, Agent, or Firm*—Sterne, Kessler, Goldstein & Fox PLLC; Anna M. Murphy

(57) ABSTRACT

Inactive precursor forms of PSA (pPSA) have been identified to exist in serum and tissues of patients with prostate cancer. Antibodies specific for pPSA are provided. Methods for detecting inactive precursors of PSA in human physiological fluid and tissues are also provided, as well as diagnostic kits and methods useful in the diagnosis and management of prostate cancer.

12 Claims, 12 Drawing Sheets

OTHER PUBLICATIONS

A. Kumar, et al. Expression of Human Glandular Kallikrein, hK2, in Mammalian Cells. Cancer Res., 56: 5397-5402, 1996.

S. D. Mikolajczyk, et al., "BPSA," A Specific Molecular Form of Free Prostate-Specific Antigen, Is Found Predominantly in the Transition Zone of Patients with Nodular Benign Prostatic Hyperplasia. Urology, 55: 41-45, 2000.

T. J. Wang, et al., Benign Prostatic Hyperplasia-Associated Prostate-Specific Antigen (BPSA) Shows Unique Immunoreactivity with Anti-PSA Monoclonal Antibodies. Eur.J.Biochem., 267: 4040-4045, 2000.

C. K. Naughton, et al., Clinical and Pathologic Tumor Characteristics of Prostate Cancer As A Function of the Number of Biopsy Cores: A Retrospecitve Study. Urology, 52: 808-813, 1998.

J. Lövgren, et al., Activation of the Zymogen Form of Prostate-Specific Antigen by Human Glandular Kallikrein 2. JBiol.Biophys. Res. Comm., 238: 549-555, 1997.

T. K. Takayama, et al., Characterization of the Precursor of Prostate-specific Antigen [Activation by Trypsin And by Human Glandular Kallikerin]. J.Biol.Chem., 272: 21582-21588, 1997.

M. F. Darson, et al., Human Glandular Kallikrein 2 (hK2) Expression in Prostatic Intraepithelial Neoplasia and Adenocarcinoma: A Novel Prostate Cancer Marker. Urology, 49(6): 857-862, 1997.

S. D. Mikolajczyk, et al., A Precursor Form of Prostate-specific Antigen Is More Highly Elevated in Prostate Cancer Compared with Benign Transition Zone Prostate Tissue. Cancer Res., 60: 756-759, 2000.

W. J. Catalona, Clinical Utility of Measurements of Free and Total Prostate-Specific Antigen (PSA): A Review. Prostate, *Supplement 7*: 64-69, 1996.

Mikolajczyk, S.D., et al., "A truncated precursor form of prostate-specific antigen is a more specific serum marker of prostate cancer," *Cancer Research* vol. 61, 18:6958-6963 (Sep. 15, 2001).

Peter, J., et al., "Identification of precursor forms of free prostate-specific antigen in serum of prostate cancer patients by immunosorption and mass spectrometry," *Cancer Research* vol. 61, 3:957-962 (Feb. 1, 2001).

Hill, T., et al., "Development of PROhK2 Specific Assay," *Tumor Biol. 18*:7, Karger (1997).

Karr, J.F., et al., "The Presence of Prostate-specific Antigen-related Genes in Primates and the Expression of Recombinant Human Prostate-specific Antigen in a Transfected Murine Cell Line," *Cancer Res. 55*:2455-2462, American Association for Cancer Research, Inc. (1995).

Kurkela, R., et al., "Expression of Active, Secreted Human Prostate-specific Antigen by Recombinant Baculovirus-infected Insect Cells on a Pilot-scale," *Biotechnology 13*:1230-1234, Nature Publishing Co. (1995).

Lövgren, J., et al., "Production of Recombinant PSA and hK2 and Analysis of Their Immunologic Cross-Reactivity," *Biochem. Biophys. Res. Comm. 213*:888-895, Academic Press, Inc. (1995).

Pettersson, K., et al., "Free and Complexed Prostate-Specific Antigen (PSA): In Vitro Stability, Epitope Map, and Development of Immunofluorometric Assays for Specific and Sensitive Detection of Free PSA and PSA-$\alpha_1$-Antichymotrypsin Complex," *Clin. Chem. 41*:1480-1488, American Association for Clinical Chemistry, Inc. (1995).

Charlesworth, M.C., et al., "Detection of a Prostate-Specific Protein, Human Glandular Kallikrein (hK2), in Sera of Patients with Elevated Prostate-Specific Antigen Levels," *Urology 49*:487-493, Elsevier Science Inc. (1997).

Kumar, A., et al., "Expression of Human Glandular Kallikrein, hK2, in Mammalian Cells," *Cancer Res. 56*:5397-5402, American Association for Cancer Research (1996).

McCormack, R.T., et al., "Molecular Forms of Prostate-Specific Antigen and the Human Kallikrein Gene Family: A New Era," *Urology 45*:729-744, Elsevier Science (1995).

Japanese Office Action, Patent Application No. 10-547269, mailed on Oct. 14, 2008, 6 pages.

English language translation of Japanese Office Action, Patent Application No. 10-547269, mailed on Oct. 14, 2008, 5 pages (listed on accompanying PTO/SB/08B as NPL11).

Dialog File 351, Accession No. 7344186, English language abstract for JP 6343476 A (listed on accompanying PTO/SB/08A as FP6).

Dialog File 351, Accession No. 6192703, English language abstract for JP 6502719 W (listed on accompanying PTO/SB/08A as FP7).

Dialog File 351, Accession No. 7357344, English language abstract for JP 9501152 W (listed on accompanying PTO/SB/08A as FP8).

Dialog File 351, Accession No. 7906764, English language abstract for JP 11503515 W (listed on accompanying PTO/SB/08A as FP9).

Dialog File 351, Accession No. 7911969, English language abstract for JP 11505111 W (listed on accompanying PTO/SB/08A as FP10).

\* cited by examiner

| | A BIOPSY | | B BIOPSY | |
|---|---|---|---|---|
| | (+) | (−) | (+) | (−) |
| ng/ml TOTAL PSA | 9.9 | 10.4 | 6.2 | 6.9 |
| % FREE PSA | 9% | 28% | 19% | 15% |
| [−2]pPSA → | | | | |
| [−2]pPSA | 40% | 8% | 25% | 6% |
| BPSA | 5% | 25% | 14% | 13% |
| pPSA/BPSA | 8 | 0.32 | 1.8 | 0.46 |

```
SEQUENCE LISTING

<160> NUMBER OF SEQ ID NOS: 7

<210> SEQ ID NO 1
<211> LENGTH: 90
<212> TYPE: DNA
<213> ORGANISM: Homo sapiens

<400> SEQUENCE: 1
atgtgggtcc cggttgtctt cctcaccctg tccgtgacgt ggattggcgc tgcgccctc     60 atcctgtctc ggattgtggg aggctgggag                                     90

<210> SEQ ID NO 2
<211> LENGTH: 30
<212> TYPE: PRT
<213> ORGANISM: Homo sapiens

<400> SEQUENCE: 2

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu
            20                  25                  30

<210> SEQ ID NO 3
<211> LENGTH: 11
<212> TYPE: PRT
<213> ORGANISM: Homo sapiens

<400> SEQUENCE: 3

Ser Arg Ile Val Gly Gly Trp Glu Cys Glu Lys
1               5                   10

<210> SEQ ID NO 4
<211> LENGTH: 13
```

```
<212> TYPE: PRT
<213> ORGANISM: Homo sapiens

<400> SEQUENCE: 4

Ile Leu Ser Arg Ile Val Gly Gly Trp Glu Cys Glu Lys
1               5                   10

<210> SEQ ID NO 5
<211> LENGTH: 9
<212> TYPE: PRT
<213> ORGANISM: Homo sapiens

<400> SEQUENCE: 5

Ile Val Gly Gly Trp Glu Cys Glu Lys
1               5

<210> SEQ ID NO 6
<211> LENGTH: 7
<212> TYPE: PRT
<213> ORGANISM: Homo sapiens

<400> SEQUENCE: 6

Ala Pro Leu Ile Leu Ser Arg
1               5

<210> SEQ ID NO 7
<211> LENGTH: 5
<212> TYPE: PRT
<213> ORGANISM: Homo sapiens

<400> SEQUENCE: 7

Leu Ile Leu Ser Arg
1               5
```

FORMS OF PROSTATE SPECIFIC ANTIGENS AND METHODS FOR THEIR DETECTION

This is a continuation-in-part of application Ser. No. 09/302,965, filed on Apr. 30, 1999, now abandoned, which in turn is a continuation-in-part of application Ser. No. 09/251,686, filed on Feb. 17, 1999, now abandoned, which in turn is a continuation of application Ser. No. 08/846,408, filed on Apr. 30, 1997, now abandoned. The content of the applications Ser. Nos. 09/251,686, 09/302,965, and 08/846,408 are incorporated herein in their entirety by reference.

FIELD OF THE INVENTION

The present invention relates generally to the detection and identification of proteins, as well as various forms and subunits of proteins, which have the potential utility as diagnostic markers. In particular, the present invention relates to the detection of inactive precursor forms of prostate specific antigens, and antibodies that are capable of preferentially binding to precursor forms of prostate specific antigens.

BACKGROUND OF THE INVENTION

The measurement of serum prostate specific antigen (PSA) is widely used for the screening and early detection of prostate cancer[1-3]. Serum PSA that is measurable by current clinical immunoassays exists primarily as either the free "non-complexed" form (free PSA), or as a complex with $\alpha_1$-antichymotrypsin (ACT)[4,5]. The ratio of free to total PSA in serum has been demonstrated to significantly improve the discrimination of PCa from benign prostatic diseases, with higher ratios correlating with a lower risk of prostate cancer[6,7]. While benign prostate hyperplasia (BPH) is the most common benign prostatic disease it is recognized that other benign diseases such as prostatitis, prostatic infarct and prostatic injury can also elevate serum PSA and cause changes in the free to total PSA ratio.

The biological mechanism for the variable levels of free PSA in serum is unknown. The serum PSA that has become complexed is likely to be relatively homogeneous since this represents enzymatically active, intact PSA. The PSA released from the PSA-ACT complex in prostate cancer (Pca) and benign prostate hyperplasia (BPH) serum was found to be indistinguishable from seminal plasma PSA, which confirms this assumption[8]. It follows that free PSA may offer better biochemical insight, and that a characterization of the molecular forms of free PSA could help elucidate their prostatic origin and mechanism of release into the serum. However, attempts to purify and characterize the low levels of PSA from serum in the diagnostically relevant range near 10 ng/ml have not generally been considered feasible with current technologies. So far, studies have focused primarily on serum from men with unusually high levels of PSA, with 100's or 1000's of ng/ml PSA. However, other groups have failed to identify pPSA in serum containing these high levels of PSA[9, 10]. While studies using high serum PSA levels are suggestive, they suffer a common drawback in that this PSA may not reflect the kind or percentage of PSA that is typically present in the early stages of disease, where PSA is 10 ng/ml or less. PSA released from large primary tumor lesions or metastatic disease may have different biochemical properties than PSA released from early, possibly lower grade disease. Therefore, in order to be useful for clinical detection of early prostate cancer, the truncated pPSA forms would have to be present at significant levels in serum with diagnostically relevant levels of total PSA near 10 ng/ml.

Accordingly, a need exists to characterize different forms of free PSA present in prostate cancer serum with diagnostically relevant levels of total PSA near 10 ng/ml. A need also exists to determine the diagnostic potential of these pPSA forms in prostate cancer detection. In addition, since any characterization of the free PSA forms in serum must necessarily depend on the development of mAbs, a need also exists for developing antibodies that are specific for these pPSA forms.

SUMMARY OF THE INVENTION

The present invention is based on the successful expression of chimeric pPSA protein in mammalian cells. It is herein demonstrated for the first time that PSA is secreted into the spent media by mammalian cells as proPSA. The proPSA thus secreted is enzymatically inactive and stable in the media. Therefore, vectors of the present invention may be used to generate proPSA polypeptides.

Accordingly, one aspect of the present invention provides a chimeric expression vector comprising a nucleic acid molecule. The nucleic acid molecule encodes a pPSA polypeptide. The nucleic acid molecule is preferably operably linked to control sequences which are recognized by a host cell that is transformed with the expression vector. The host cell is preferably derived from a mammalian source.

ProPSA polypeptides, as well as variants and subunits thereof, produced by the methods of the present invention can be used to produce populations of antibodies that are specific for proPSA, particularly different forms of proPSA. Because of the minor structural differences between pPSA and PSA, the development of pPSA-specific mAbs has been extremely difficult in the past. Mature PSA contains at least 6 major antigenic epitopes[11] that induce a strong immune response in mice, and obscures the development of pPSA recognition. In the literature, efforts specifically designed to generate pPSA mAbs have yielded no suitable mAbs[12]. In the present invention, due to the successful expression of chimeric pPSA protein, antibodies specific for pPSA may be generated by utilizing purified pPSA peptides and thus minimizing an interfering PSA immune response. In addition, the present invention also focuses on developing antibodies that detect different truncated pPSA forms.

Thus, one aspect of the present invention provides an antibody, preferably a monoclonal antibody, which specifically binds to proPSA. Antibodies to the various inactive precursor forms of proPSA, including, but not limited to [−2], [−4] pPSA, [−5]pPSA and [−7]pPSA, are also contemplated. Antibodies of the present invention are not only specific for the pPSA region of the pPSA protein, but also capable of detecting the even more subtle differences between [−7], [−4] and [−2]pPSA forms.

The present invention also encompasses a method for detecting proPSA in a human tissue or physiological fluid. This aspect of the invention is based on the discovery that proPSA exists stably in biological fluid as part of free PSA and may serve as a useful marker for prostate cancer. Specifically, several inactive precursor forms of PSA, such as, but not limited to [−2], [−4] and [−7]pPSA forms, have been identified and detected in serum. In accordance with the present invention, the identified precursor forms of PSA do not form a complex with ACT and exist as stable and free PSA in serum. The measurement of these inactive precursor forms of PSA may provide important information regarding the detection, monitoring and staging of prostate cancer.

Therefore, proPSA polypeptides, as well as variants and subunits thereof, produced by the methods of the present invention can be used to produce populations of antibodies that, in turn, can be used as the basis for direct or competitive assays to detect and quantify proPSA polypeptides (or "protein") in samples derived from physiological fluids, such as seminal fluid, blood or serum; tissues, such as prostate carcinomas; or cells, such as prostate cells.

Direct and competitive assays to detect proPSA are also included within the scope of the present invention. A method for detecting proPSA in a sample of human physiological fluid is described which includes providing purified antibodies to pPSA, contacting the antibodies with the sample to allow formation of complexes between the antibodies and pPSA, and determining the presence or amount of pPSA complexed with the antibodies.

Using the antibodies and immunoassays of the present invention, it is discovered that different pPSA forms exist in serum, and that the [−2]pPSA is the most prevalent form. It is also a surprise discovery of the present invention that [−2] pPSA comprises a significant percentage of the free PSA in prostate cancer serum.

Accordingly, based on the discoveries of the present invention, one aspect of the present invention provides diagnostic methods for detecting and/or determining the presence of prostate cancer in a subject, or for distinguishing prostate cancer from non-cancer benign disease in a subject. In accordance with embodiments of the present invention, such a method includes the steps of determining the amount of pPSA contained in a sample of the subject, and correlating the amount of pPSA to the presence of prostate cancer in the subject.

Kits for detecting or distinguishing prostate cancer from benign disease are also included as embodiments of the present invention.

BRIEF DESCRIPTION OF THE DRAWINGS

FIG. 4 depicts the HIC chromatographic profile of the different forms of PSA.

FIG. 5 depicts the chromatographic profile for a mixture of purified mature PSA and pPSA.

DETAILED DESCRIPTION OF THE PREFERRED EMBODIMENTS

Figure 1:
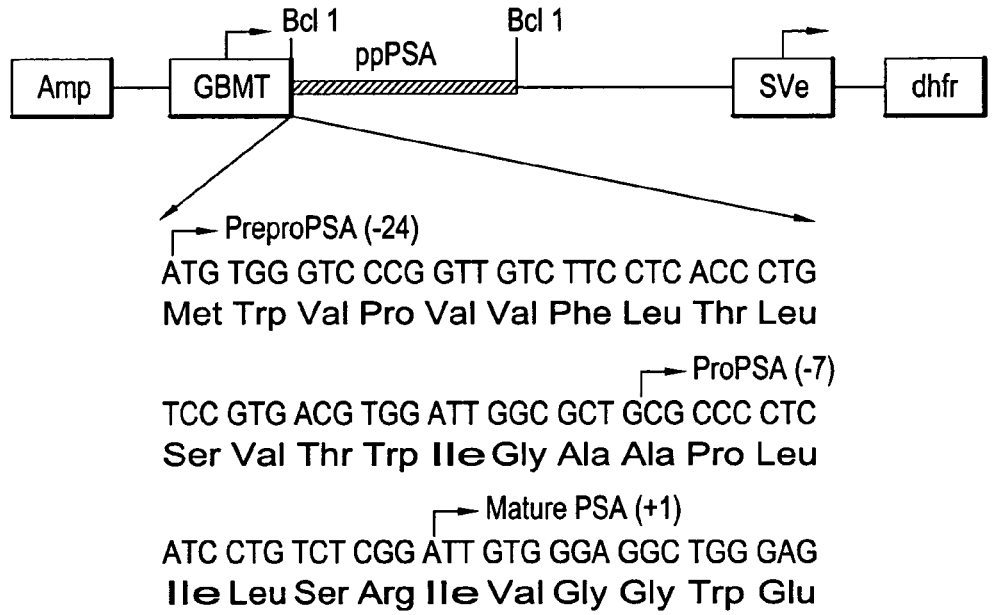
FIG. 1 is a schematic representation of PSA expression vector, pGTD-PSA.

The identification of inactive precursor forms of PSA in serum suggests that measuring serum concentrations of proPSA can be useful in the detection and monitoring of prostate cancer. In order to discern the steps involved in the biosynthesis of PSA and the activation of proPSA to mature PSA, the expression of PSA in mammalian cells is necessary. The details of expressing PSA in mammalian cells are provided in the copending U.S. patent applications, Ser. Nos. 09/251,686 and 09/302,965, the content of which is incorporated herein in its entirety by reference.

As used herein, the terms "PSA" and "PSA polypeptide" are used interchangeably and include recombinant prepro, pro, and mature PSA polypeptides. The terms "proPSA," "pPSA," "proPSA polypeptide", and "pPSA polypeptide" are used interchangeably and preferably encompass all inactive precursor forms of PSA, including, but not limited to, [−2] proPSA, [−4]proPSA, [−7]proPSA, and [−5]proPSA.

As used herein, "chimeric" means that a vector comprises DNA from at least two different species, or comprises DNA from the same species, which is linked or associated in a manner which does not occur in the "native" or wild type of the species.

"Control sequences" is defined to mean DNA sequences necessary for the expression of an operably linked coding sequence in a particular host organism. The control sequences that are suitable for prokaryotic cells, for example, include a promoter and, optionally, an operator sequence and a ribosome binding site. Eukaryotic cells are known to utilize promoters, polyadenylation signals and enhancers.

"Operably linked" means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Press (2d ed., 1989) provides suitable methods of construction.

The recombinant DNA can be readily introduced into the target cells by transfection with an expression vector comprising cDNA encoding PSA, for example, by the modified calcium phosphate precipitation procedure of C. Chen et al., *Mol. Cell. Biol.*, 7, 2745 (1987). Transfection can also be accomplished by lipofection, using commercially available kits, e.g., those provided by BRL Life Technologies, Inc.

Suitable host cells for the expression of PSA are derived from multicellular organisms. Such host cells are capable of complex processing and glycosylation activities. However, mammalian cells are the preferred host for expression of mammalian protein, since these cells modify and process the recombinant protein in a manner closely related to the natural host of the protein. In principle, any higher eukaryotic cell culture can be employed in the practice of the invention, whether from vertebrate or invertebrate culture. Examples of invertebrate cells include plant and insect cells. Numerous baculoviral strains and variants and corresponding permissive insect host cells have been identified.

"Polymerase chain reaction," or "PCR," refers to a procedure or technique in which amounts of a preselected fragment of nucleic acid, RNA and/or DNA, are amplified as described in U.S. Pat. No. 4,683,195. Generally, sequence information from the ends of the region of interest or beyond are employed to design oligonucleotide primers. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See, generally, Mullis et al., *Cold Spring Harbor Symp. Quant. Biol.*, 51, 263 (1987); Erlich, ed., *PCR Technology* (Stockton Press, NY, 1989).

When a PSA polypeptide is expressed in a recombinant cell other than one of human origin, the PSA polypeptide is completely free of proteins or polypeptides of human origin. However, it is necessary to purify PSA polypeptides from recombinant cell proteins or polypeptides to obtain preparations that are substantially homogeneous as to PSA polypeptides. For example, the culture medium or lysate can be centrifuged to remove particulate cell debris. The membrane and soluble protein fractions are then separated. The PSA polypeptide may then be purified from the soluble protein fraction and, if necessary, from the membrane fraction of the culture lysate. The PSA polypeptide can then be purified from contaminant soluble proteins and polypeptides by fractionation on immunoaffinity or ion exchange columns; ethanol precipitation; reverse phase HPLC; chromatography on silica or on an anion exchange resin such as DEAE; chromatofocusing; SDS-PAGE; ammonium sulfate precipitation; gel filtration using, for example, SEPHADEX G-75; or ligand affinity chromatography.

Once isolated, and in accordance with an embodiment of the present invention, a proPSA polypeptide or peptide corresponding to the proPSA region can be used to produce anti-pPSA antibodies. The proPSA polypeptides used to generate antibodies in accordance with the invention include, but are not limited to, −7, −5, −4 and −2 proPSA. Peptides corresponding to the proPSA region can also be used to generate anti-pPSA antibodies and include all peptides which contain any portion of the pro region of the pPSA polypeptide. These peptides preferably contain about 8 to 15 amino acids and comprise an immunogenic epitope.

In accordance with one embodiment of the present invention, pro peptide(SEQ ID NO:3) SRIVGGWECEK may be used to generate antibodies for [−2]proPSA. Pro peptide (SEQ ID NO:4) ILSRIVGGWECEK may be used to generate antibodies for [−4]proPSA. The purified recombinant protein consisting of the PSA prepro leader peptide may be used to generate antibodies for [−7]proPSA.

In accordance with the present invention, an antibody which consists essentially of pooled monoclonal antibodies with different epitopic specificities, as well as distinct monoclonal antibody preparations, is provided. Monoclonal antibodies against purified pPSA (total protein) or the above peptides can be prepared using known hybridoma cell culture techniques, for example, as described by E. Harlow et al., *Antibodies: A Laboratory Manual*, Cold Spring Harbor Laboratory, 1988. In general, this method involves preparing an antibody-producing fused cell line, e.g., of primary spleen cells fused with a compatible continuous line of myeloma cells, and growing the fused cells either in mass culture or in an animal species from which the myeloma cell line used was derived or is compatible. Such antibodies offer many advantages in comparison to those produced by the inoculation of animals, as they are highly specific and sensitive and relatively "pure" immunochemically. Immunologically active fragments of antibodies are also within the scope of the present invention, e.g., the f(ab) fragment, as are partially humanized monoclonal antibodies.

If desired, polyclonal antibodies can be further purified, for example, by binding to an elution from a matrix to which a polypeptide, or a peptide to which the antibodies were raised, is bound. Those skilled in the art will know of various techniques common in the immunology arts for purification and/or concentration of polyclonal antibodies, as well as monoclonal antibodies. (See, for example, Coligan et al., Unit 9, *Current Protocols in Immunology*, Wiley Interscience, 1991, incorporated by reference.)

The term "antibody" as used in this invention includes intact molecules as well as fragments thereof, such as Fab, $F(ab')_2$, and Fv, which are capable of binding the epitopic determinant. These antibody fragments retain some ability to selectively bind with their antigen or receptor.

Accordingly, one aspect of the present invention provides an antibody that specifically binds to proPSA of the present invention. The term "specifically immunoreactive or specifically binds to" as used herein indicates that the antibodies of the present invention recognize and bind to antigenic determinants or epitopes that are unique to proPSA, and are not found on mature PSA. Examples of monoclonal antibodies that specifically bind to proPSA include, but are not limited to, PS2P206, PS2P309, PS2P446, PS2P031, PS2P401, PS2P167, PS2P125, PS2P134, PS2X094, PS2X373, PS2X199, PS2X458, PS2X572, PS2V411, and PS2V476. For example, monoclonal antibody PS2P446 is specific for [−7] and/[−4]pPSA by Western blot analysis, though specific for [−7]pPSA by immunoassay. PS2X373 is specific for [−2] pPSA. PS2V476 is specific for [−4]pPSA.

Antibodies of the present invention may be used for detecting and determining the presence and amount of proPSA in a sample. They may also be used for detecting and determining the presence and amount of different forms of proPSA in a sample. In accordance with the present invention, the proPSA may be detected in patient tissue samples by immunohistochemical methods and/or in patient fluid samples by in vitro immunoassay procedures.

Immunohistochemical methods for the detection of antigens in patient tissue specimens are well-known in the art and need not be described in detail herein. For example, methods for the immunohistochemical detection of antigens are generally described in Taylor, *Arch. Pathol. Lab. Med.* 102:113 (1978). Briefly, in the context of the present invention, a tissue specimen obtained from a patient suspected of having a prostate-related problem is contacted with an antibody, preferably a monoclonal antibody, recognizing proPSA. The site at which the antibody is bound is thereafter determined by selective staining of the tissue specimen by standard immunohistochemical procedures. In one embodiment of the present invention, the tissue specimen is a tissue specimen obtained from the prostate of a patient. The prostate tissue may be a normal or benign prostate tissue, a cancer prostate tissue, or a benign prostatic hyperplasia tissue.

Similarly, the general methods of the in vitro detection of antigenic substances in patient fluid samples by immunoassay procedures are also well-known in the art and require no repetition herein. For example, immunoassay procedures are generally described in Paterson et al, *Int. J. Can.* 37:659 (1986) and Burchell et al., *Int. J. Can.* 34:763 (1984). According to one embodiment of the present invention, an immunoassay for detecting proPSA in a biological sample comprises the steps of: (a) contacting an antibody that specifically binds to proPSA with the sample under a condition that allows a formation of a binary complex comprising the proPSA and the antibody; and (b) detecting and determining the amount of the complex.

For the purpose of the present invention, the biological sample can be any human physiological fluid sample that contains proPSA of the present invention. Examples of the human physiological fluid sample include, but are not limited to, blood, serum, seminal fluid, urine, and plasma.

For the purpose of the present invention, both monoclonal antibodies and polyclonal antibodies may be used as long as such antibodies possess the requisite specificity for the antigen provided by the present invention. Preferably, monoclonal antibodies are used.

Monoclonal antibodies can be utilized in a liquid phase or bound to a solid phase carrier. Monoclonal antibodies can be bound to many different carriers and used to determine the proPSA of the present invention. Examples of well-known carriers include glass, polystyrene, polypropylene, polyethylene, dextran, nylon, amylases, natural and modified celluloses, polyacrylamides, agaroses, and magnetites. The nature of the carrier can be either soluble or insoluble for purposes of the invention. Examples of insoluble carriers include, but are not limited to, a bead and a microtiter plate. Those skilled in the art will know of other suitable carriers for binding monoclonal antibodies or will be able to ascertain such under routine experimentation.

In addition, the monoclonal antibodies in these immunoassays can be detectably labeled in various ways. For example, monoclonal antibodies of the present invention can be coupled to low molecular weight haptens. These haptens can then be specifically detected by means of a second reaction. For example, it is common to use such haptens as biotin, which reacts with avidin, or dinitrophenyl, pyridoxal and fluorescein, which can react with specific antihapten antibodies. In addition, monoclonal antibodies of the present invention can also be coupled with a detectable label such as an enzyme, radioactive isotope, fluorescent compound or metal, chemiluminescent compound, or bioluminescent compound. Furthermore, the binding of these labels to the desired molecule can be done using standard techniques common to those of ordinary skill in the art.

One of the ways in which the antibody can be detectably labeled is by linking it to an enzyme. This enzyme, in turn, when later exposed to its substrate, will react with the substrate in such a manner as to produce a chemical moiety which can be detected by, for example, a spectrophotometric or fluorometric means (ELISA system). Examples of enzymes that can be used as detectable labels are horseradish peroxidase, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase, and acetylcholine esterase.

For increased sensitivity in the ELISA system, the procedures described can be modified using biotinylated antibodies reacting with avidin-peroxidase conjugates.

The amount of antigen can also be determined by labeling the antibody with a radioactive isotope. The presence of the radioactive isotope would then be determined by such means as the use of a gamma counter or a scintillation counter. Isotopes which are particularly useful are $^{3}H$, $^{125}I$, $^{123}I$, $^{32}P$, $^{35}S$, $^{14}C$, $^{51}Cr$, $^{36}Cl$, $^{57}Co$, $^{58}Co$, $^{59}Fe$, $^{75}Se$, $^{111}N$, $^{99}mTc$, $^{67}Ga$, and $^{90}Y$.

Determination of the antigen is also possible by labeling the antibody with a fluorescent compound. When the fluorescently labeled molecule is exposed to light of the proper wave length, its presence can then be detected due to fluorescence of the dye. Among the most important fluorescent labeling compounds are fluorescein isothiocyanate, rhodamine, phycoerythrin, phycocyanin, allophycocyanin, o-phthaldehyde, and fluorescamine.

Fluorescence-emitting metal atoms, such as Eu (europium), and other lanthanides, can also be used. These can be attached to the desired molecule by means of metal-chelating groups, such as DTPA or EDTA.

Another way in which the antibody can be detectably labeled is by coupling it to a chemiluminescent compound. The presence of the chemiluminescent-tagged immunoglobulin is then determined by detecting the presence of luminescence that arises during the course of a chemical reaction. Examples of particularly useful chemiluminescent labeling compounds are luminol, isoluminol, aromatic acridinium ester, imidazole, acridinium salt, and oxalate ester.

Likewise, a bioluminescent compound may also be used as a label. Bioluminescence is a special type of chemiluminescence which is found in biological systems in which a catalytic protein increases the efficiency of the chemiluminescent reaction. The presence of a bioluminescent molecule would be determined by detecting the presence of luminescence. Important bioluminescent compounds for purposes of labeling are luciferin, luciferase, and aequorin.

Qualitative and/or quantitative determinations of proPSA of the present invention in a sample may be accomplished by competitive or non-competitive immunoassay procedures in either a direct or indirect format. Examples of such immunoassays are the radioimmunoassay (RIA) and the sandwich (immunometric) assay. Detection of the antigens using the monoclonal antibodies of the present invention can be done utilizing immunoassays which are run in either the forward, reverse, or simultaneous modes, including immunohistochemical assays on physiological samples. Those skilled in the art will know, or can readily discern, other immunoassay formats without undue experimentation.

The terms "immunometric assay" or "sandwich immunoassay" include a simultaneous sandwich, forward sandwich, and reverse sandwich immunoassay. These terms are well understood by those skilled in the art. Those skilled in the art will also appreciate that antibodies according to the present invention will be useful in other variations and forms of assays which are presently known or which may be developed in the future. These are intended to be included within the scope of the present invention.

As well as being useful as an antigen to produce the present anti-pPSA antibodies, the isolated pPSA polypeptide produced in accordance with a method of the present invention and its antigenically active variants, derivatives, and fragments thereof can be used in assays for proPSA in samples derived from biological materials suspected of containing proPSA or anti-proPSA antibodies.

A useful immunoassay which can be practiced in accordance with an embodiment of the present invention is the two-antibody sandwich technique. These assays are used primarily to determine the antigen concentration in unknown samples. Two-antibody assays are quick and accurate, and if a source of pure antigen (in this case, proPSA) is available, the assays can be used to determine the absolute amounts of antigen in unknown samples. The assay requires two antibodies that bind to non-overlapping epitopes on the antigen. Either two monoclonal antibodies that recognize discrete sites or one batch of affinity-purified polyclonal antibodies can be used.

In a two-antibody assay, one antibody is purified and bound to a solid phase. Any solid phase can be used; however, for most applications, a PVC microtiter plate is preferred. The bound antibody (to a well of a microtiter plate, for example) is unlabeled and is referred to as the "capture antibody." The amount of antibody to be used will depend on the individual assay, but an amount of about 1 µg/well generally gives maximal binding. Higher or lower amounts of capture antibody can also be used. The wells can then be washed and sample added to the wells to allow the antigen (in this case, pPSA) in the test solution to bind to the solid phase. Unbound proteins can be removed by washing and a labeled second antibody can be added. Alternatively, the sample and the second labeled antibody can be added simultaneously. After washing, the assay can be quantitated by measuring the amount of labeled second antibody that is bound to the solid phase. A most preferred embodiment of the present invention utilizes a monoclonal antibody as the first unlabeled antibody and a monoclonal antibody as the second labeled antibody. The detection method used to quantitate the amount of bound labeled antibody depends on the label used. Antibodies can be labeled conveniently with iodine, enzymes, or biotin. Calorimetric or other detection methods can be used.

The proPSA polypeptides of the present invention can be immobilized and used as "capture antigens" to bind and immobilize anti-pPSA antibodies from a sample to be assayed for anti-pPSA antibodies. The bivalent complex of proPSA polypeptides and anti-pPSA antibodies is then detected, e.g., in the case of human physiological material, by reacting it with an anti-human IgG antibody which comprises a detectable label or a binding site for a detectable label. In the latter case, the binding site is itself reacted with a compound specific for the binding site, which itself comprises a detectable label. Useful detectable labels include enzymes, radio labels, or fluorescent labels. The resultant ternary or quaternary complex can then be detected and/or quantified via the detectable label, i.e., via an enzyme-substrate color-forming reaction, radio emission, agglomeration, and the like.

Alternatively, the proPSA polypeptide can be labeled with a detectable label, such as via one or more radio labeled peptidyl residues, and can be used to compete with endogenous proPSA for binding to anti-proPSA antibodies, i.e., as a capture antigen to bind to anti-proPSA antibodies in a sample of a physiological fluid via various competitive immunoassay formats. For example, a competitive immunoassay for proPSA which uses immobilized anti-proPSA antibodies is carried out by:

(a) providing an amount of proPSA specific antibodies attached to a solid surface;

(b) mixing the sample of physiological fluid to be tested with a known amount of proPSA polypeptide which comprises a detectable label to produce a mixed sample;

(c) contacting said antibodies with said mixed sample for a sufficient time to allow immunological reactions to occur between said antibodies and said proPSA to form an antibody-proPSA complex, and between said antibodies and said labeled polypeptide to form an antibody-labeled polypeptide complex;

(d) separating the antibodies which are bound to proPSA and antibodies bound to the labeled polypeptide from the mixed sample;

(e) detecting or determining the presence or amount of labeled polypeptide either bound to the antibodies on the solid surface or remaining in the mixed sample; and (f) determining from the result in step (e) the presence or amount of said proPSA in said sample.

The immunoassays of the present invention may be used to detect pPSA in human physiological samples, such as serum and tissue, for the purpose of detecting and monitoring prostate cancer. The assays of the present invention may also be used to distinguish prostate cancer from begnign prostate disease, such as benign prostatic hyperplasia.

It is a discovery of the present invention that pPSA, i.e., [−2] and [−4]pPSA, are present in prostate cancer serum and tissues. Particularly, it is a surprise discovery of the present invention that [−2]pPSA is not only present in prostate cancer serum, but is found more consistently, and comprises a major percentage of the free PSA. More importantly, it is a discovery of the present invention that the major percentage of the free PSA is [−2]pPSA in the prostate cancer serum of men with total PSA values from 6-24 ng/ml. Therefore, pPSA, particularly [−2]pPSA, represents a significant and relevant isoform of PSA for the study of prostate cancer. It is in the range below 10 ng/ml where it is most difficult to discriminate prostate cancer from benign conditions such as BPH since both conditions release PSA into the serum[13,14]. In addition, while the [−4] and [−7]pPSA forms appear to be absent in some samples of the limited serum group tested, it is possible each of these forms may show specific utility in a larger group. Therefore, [−2]pPSA, or other pPSA forms could offer the greatest diagnostic value as the percentage of total PSA, as a percentage of the free PSA, or as an independent indicator where pPSA levels above a certain threshold have a high statistical correlation with cancer. In the latter case, the presence of pPSA could offer diagnostic value in serum containing any measurable level of pPSA, and especially in serum with less than 4 ng/ml total PSA.

Accordingly, the present invention provides a diagnostic method for detecting or determining the presence of the prostate cancer in a subject. In accordance with the embodiments of the present invention, a diagnostic method of the present invention may include the steps of determining the amount of pPSA in a sample of the subject, and correlating the amount of the pPSA to the presence of prostate cancer. In accordance with one embodiment of the present invention, pPSA may be [−2], [−4], and/or [−7]pPSA. In one embodiment, pPSA is [−2]pPSA.

The amount of pPSA may be measured by any method described herein or known in the art, or later developed, as long as they are capable of making such a measurement. In accordance with one embodiment of the present invention, pPSA contained in a sample may be measured by a method including the steps of contacting an antibody that binds with sufficient specificity to proPSA in the sample under a condition that allows the formation of a binary complex comprising the proPSA and the antibody, and detecting and determining the amount of the complex.

For the purpose of the present invention, the binding of an antibody to pPSA is sufficiently specific if the antibody can be practically used to achieve the discrimination between pPSA and other forms of PSA, and therefore to allow the detection and determination of the amount of pPSA in a given application and format. Examples of such antibodies include, but not limited to, antibodies that are specific for pPSA, and antibodies that preferentially bind to pPSA. In addition, not only antibodies specifically or preferentially bind to a particular form, forms of pPSA, but also antibodies that specifically or preferentially bind to all forms of pPSA are contemplated. An example of such an antibody that specifically or preferentially binds to all forms of pPSA would be an antibody that detects either [−1] or [−2]pPSA but also detects pPSA containing additional pro leader amino acids from [−3] through [−7].

The term "preferentially bind to" as used herein indicates that the antibody binds to pPSA to a greater extent than binding to other forms of PSA. The degree or extent to which these antibodies recognize proPSA better than other PSA forms will depend upon the specific application and format employed. The evaluation and selection of antibodies with preferential binding is well known to those skilled in the art and is a routine part of development of any immunoassay. The term "other forms of PSA" as used herein include any forms of PSA that are not pPSA, such as other clipped or non-clipped mature forms of PSA. Examples of antibodies that preferentially bind to pPSA include, but are not limited to PS1Z134, PS1Z120, PS1Z125, and PS1Z80.

In addition, any equivalents of the above discussed antibodies may also be used for measuring the amount of pPSA. For the purpose of the present invention, any molecular species, known or developed later, capable of binding to pPSA with sufficient specificity will be considered as equivalents of the antibodies, and therefore may be used for measuring the amount of pPSA. Such equivalents of the antibodies may be selected by methods known in the art. For example, any known binding assays may be used to determine the binding activity of any given molecule. . Examples of potential molecular species include, but are not limited to, antigen-binding fragments derived from antibodies, and aptamers.

In accordance with embodiments of the present invention, the antibody is an antibody specific for pPSA. For example, any antibodies described herein that are specific for pPSA may be used in the diagnostic method of the present invention. In accordance with another embodiment of the present invention, the antibody is an antibody that preferentially recognize pPSA. Examples of such antibodies include PS1Z134, PS1Z120, PS1Z125, and PS1Z80.

For the purpose of the present invention, the amount of pPSA detected in a sample of a patient may be correlated to the presence of prostate cancer in any way that generates diagnostic value for determining the presence of prostate cancer. For example, the amount of pPSA contained in a sample may be compared to the total PSA, the free PSA, the BPSA, or hK2 of a sample. The comparison, i.e., a mathematical combination, such as a ratio with other forms of PSA or hK2, or the amount of pPSA alone may be used as an indicator where pPSA levels above a pre-determined threshold have a high statistical correlation with cancer. For example, the amount of pPSA may be compared to other forms of PSA or hK2 to generate a numerical result, wherein a result above a pre-determined value is an indication of the presence of prostate cancer. For the purpose of the present invention, the term "mathematical combination" includes any mathematical combination that may generate a numerical result for determining the presence of prostate cancer. While a ratio may be the simplest mathematical combination, other more complicated forms such as polynomials, log-logic functions and artificial neural networks can also be used. These forms and others are well known to mathematicians and biostatisticians.

In view of the teaching of the present invention, one skilled in the art through routine experimentation can readily determine the cut-off values (the threshold) or other analytical parameters necessary to use the above-discussed numerical results such as a ratio or the amount of pPSA alone as a marker in determining the presence of prostate cancer. For example, one may compare the above-discussed ratio or pPSA in individuals diagnosed with prostate cancer with individuals that do not have prostate cancer or have BPH to determine the cut-off values with required specificity and sensitivity. Then the ratio or the amount of pPSA of a sample may be compared to the pre-determined cut-off value for determining the presence of prostate cancer in a subject, wherein the higher level of pPSA may be an indication of prostate cancer. The method of determining the cut-off value with required specificity and sensitivity are well known in the art, and need not be repeated$^{32-39}$.

In addition, it is a discovery of the present invention that pPSA, particularly [−2]pPSA is elevated in the serum and the tissues of prostate cancer patients when compared to its amount in the serum or the tissues of men with benign prostatic disease such as BPH. Therefore, the above-discussed ratio or the amount of the pPSA independently may also be used to determine whether a subject has a greater likelihood of prostate cancer rather than benign disease such as BPH. For example, one may examine the levels of pPSA in patients diagnosed with prostate cancer and in patients diagnosed with benign disease to determine a cut-off value. Then the ratio or amount of pPSA of an unknown patient sample may be compared to the pre-determined cut-off value, wherein the higher level of pPSA compared to the pre-determined cut-off value is an indication of prostate cancer.

Methods of measuring total PSA and free PSA are well-known in the art, and therefore will not be repeated herein. For the purpose of the present invention the term "total PSA" refers to total immunologically detectable PSA. Immunologically detectable PSA is generally the sum of the free uncomplexed PSA and the complexed PSA. Complexed PSA is primarily composed of PSA-ACT with lesser amounts of complexes with inhibitors other than ACT. Total PSA is measurable by commercially available assays such as the Hybritech® PSA assay for the ACCESS® immunoassay system. The term "free PSA" as used herein refers to enzymatically inactive PSA that circulates in blood unbound to any protease inhibitor. Free PSA is measurable by commercially available assays such as the Hybritech® free PSA assay for the ACCESS® immunoassay system. BPSA and methods of measuring BPSA are fully described in the commonly owned co-pending U.S. patent application Ser. Nos. 09/303,208 and 09/303,339, the relevant content of which is incorporated herein in its entirety by reference. Briefly, BPSA refers to a form of PSA that comprises at least one clip at Lys 182 of the amino acid sequence of a mature form of PSA. In other words, a BPSA of the present invention has the same amino acid sequence of a mature form of PSA, except that the polypeptide chain of the PSA of the present invention has been hydrolyzed between residues 182 and 183. It is discovered that while proPSA is elevated in the tissues or the serum of a prostate cancer patient, BPSA is elevated in the tissues or the serum of a patient with BPH. Therefore, by comparing proPSA with BPSA of a patient, one may distinguish prostate cancer from BPH and determine the presence of prostate cancer.

Antibodies of the present invention may also be used in a diagnostic kit for determining the presence of pPSA contained in a sample. Accordingly, one aspect of the present invention provides a kit for determining pPSA in a sample. The kit comprises a known amount of an antibody specific for pPSA. The kit may also comprise a solid support or additional known amount of antibodies specific for pPSA. Antibodies contained in the kit may be attached to a solid support, or may be detectably labeled, or both repsectively.

The invention is further described by reference to the following detailed examples.

EXAMPLES

Materials and Methods

Expression Vector Cell Line and Transfection

An 0.8-kb DNA fragment which has a nucleic acid sequence of SEQ ID. NO: 1, as set forth in FIG. 1, coding for entire ppPSA (SEQ ID NO:2) was cloned into the Bcl1 site of pGT-d under the control of GBMT promoter[15] resulting in the expression vector pGTD-PSA (FIG. 1). The orientation and the sequence of the insert was confirmed. AV12-664 (ATCC CRL 9595), cultured in DMEM (high glucose) and 10% FETAL CLONE (Hyclone, Logan, Utah), were transfected with pGTD-PSA using Lipofectamine (Life Technologies, Inc.). Transfected AV12-664 cells (AV12-PSA) were selected in 400 nM methotrexate (Sigma Chemical Company). AV12-664 transfected with the empty vector (AV12-PGTD) were also selected in a similar manner for use as a negative control. Single cell clones were isolated. Viability of cells was assessed by trypan blue dye exclusion.

Isolation of Recombinant pPSA Forms from Mammalian Cells

Recombinant PSA was expressed in mammalian AV12 and the spent media was passed over the PSA-specific mAb, PSM773. PSM773 has been shown previously to have specificity for mature, clipped, and precursor forms of PSA[16-18]. The column was washed with 40 volumes of PBS containing 0.1% reduced Triton-X 100, and bound protein eluted with 100 mM glycine pH 2.5, containing 200 mM sodium chloride. The eluant was immediately neutralized with 10% % vol/vol 1M Tris pH 8.0. The purified PSA contained no mature PSA but contained [−5/−7], [−4], and [−2]pPSA molecular isoforms of pPSA that were purified by HIC-HPLC as described below.

Immunoassay and SDS-PAGE of PSA

The concentration of PSA in serum, media, or purified preparations was determined by Tandem®-MP PSA and Tandem®-MP free PSA assays (Hybritech Incorporated, San Diego, Calif.). SDS-PAGE was performed using 4-20% gradient mini-gels (Invitrogen, Carlsbad, Calif.) under reducing or non-reducing conditions, as indicated. Samples were electroblotted onto nitrocellulose using standard procedures. Primary pPSA mAbs were used at 5 ug/ml and incubated with the blots overnight at 4° C. Blots were detected with a secondary antibody cocktail consisting of goat anti-mouse heavy and light chain-HRP 1:50,000 (Jackson Immunoresearch Laboratories, Inc., West Grove, Pa.). The immunoreactive signals were detected by SuperSignal® West Dura Extended Duration Substrate (Pierce Chemical Co., Rockford, Ill.), according to the manufacturer's instructions.

Assay for the Measurement of PSA Activity

Enzymatic activity of PSA was measured according to the procedure published by Christensson, A. et al.,[19]. Briefly, PSA preparations (either purified from seminal fluid or day 7 spent media of AV12-PSA#8 cells) were incubated with 1 mM pNA-derivatized peptide chromogenic substrates (methoxysuccinyl-Arg-Pro-Tyr-pNA, S2586; Pharmacia Hepar, Inc.) in 200 mM Tris/5 mM EDTA (pH 8.0) at 37° C. The enzymatic activity of PSA was determined by hydrolysis of the peptide chromogenic substrates, leading to an increase in absorbance at 405 nm.

HIC-HPLC of PSA

High performance hydrophobic interaction chromatography (HIC-HPLC) was performed using a polypropylaspartamide column (PolyLC, distributed by Western Analytical, Temecula, Calif.). The column was 4.6×250 mm in length with a 1000 Å pore size. Samples were applied in 1.5 M ammonium sulfate and eluted with a gradient: Buffer A: 1.2 M sodium sulfate, 25 mM sodium phosphate, pH 6.3, and Buffer B: 50 mM sodium phosphate, 5% v/v 2-propanol. The gradient was 0-35% B, 1 min, 30-80% B, 12 min, then isocratic at 80% B for 2 min before equilibration in Buffer A. High sensitivity peak detection was obtained with a Varian Model 9070 scanning fluorescence detector using an excitation of 232 nm and emission of 334 nm to detect the tryptophan residues in protein.

Purification and Detection of pPSA from Pooled Prostate Cancer Serum 75 mls of pooled human serum from prostate cancer patients with elevated PSA was obtained. Solid ammonium sulfate was added to the serum to make the final concentration 2M and then the sample was dialyzed versus 2 M ammonium sulfate for 16 hours at 4° C. The serum was then clarified by centrifugation and the supernatant solution dialyzed three times (one hour each time) against 2 liters of 20 mM sodium phosphate, pH 7. The sample was then filtered through a 0.2μ membrane filter and passed over a 0.5 ml affinity column at 1 ml/min. The affinity column consisted of the mAb PSM773 covalently bound to AMINOLINK (Pierce) resin at a concentration of 5 mg mAbs per ml of resin.

The affinity column was washed with 50 mls of PBS and the PSA eluted with 3×1 ml volumes of 100 mM glycine, 0.5 M sodium chloride, pH 2.5. The eluant (3 mls) was neutralized with 300 μl of 1 M Tris, pH 8. Ammonium sulfate was added to the eluant to a final concentration of 2 M and this sample was applied to an HPLC column to be resolved by hydrophobic interaction chromatography as described above.

Development of Monoclonal Antibodies to pPSA mAbs to [−2] and [−4]pPSA were developed by mouse immunization with peptides attached to Keyhole limpet hemocyanin (Pierce Chemical Co. Rockford, Ill.). For [−2] pPSA, the pro peptide was (SEQ ID NO:3) SRIVGG-WECEK, and for [−4]pPSA, the peptide was (SEQ ID NO:4) ILSRIVGGWECEK. Hybridomas were produced by usual methodologies[20] and the antibody clones selected by reactivity to the respective peptide indicated above, and no reactivity to the control peptide for mature PSA, (SEQ ID NO:5) IVGGWECEK. The clones were further selected on their ability to recognize purified [−2] and [−4]pPSA protein on Western blots. When SDS-PAGE was run under reducing conditions, PS2X373 showed about 20% cross-reactivity to the mature PSA protein by Western blot. However, the cross-reactivity dropped to 5% or less under non-reducing conditions and so these conditions were used for the detection of [−2]pPSA in FIG. 6C.

mAbs to full length [−7]pPSA were obtained by mouse immunization with purified recombinant chimeric protein consisting of the PSA prepro leader peptide attached to human kallikrein2[21,22]. Clones were screened on their recognition of native recombinant pPSA, and no recognition of native mature PSA. These mAbs were found to recognize only [−7]pPSA by immunoassay, but to recognize both [−7] and [−4]pPSA proteins equivalently on Western blots.

Generation of Monoclonal Antibodies with Preferential Selectivity for pPSA

PSA was purified from the medium of AV12 by the use of immunoaffinity chromatography using the anti-PSA antibody PSM773 as described above. The mice were immunized once with 50 ug of blocked immunogen in CFA and twice with 25 :g of blocked immunogen in IFA. The hybridoma culture supernatant was screened for reactivity against pPSA. Hybridomas were screened by adding 50 ul of culture supernatant was added to the wells of a streptavidin microplate (Wallac, Turku, Finland) and 50 ul of biotinylated pPSA at 100 ng/ml was also added. After one hr incubation the plate was washed with PBS/0.1% tween-20, then incubated with 50 ul per well of goat anti-mouse Ig horseradish peroxidase (1:10,000) diluted in PBS/1% BSA and 0.1% tween-20. After one hr incubation, the plate was washed and developed with OPD substrate. To determine the specificity of monoclonal antibodies, the reactivity of 100 ng/ml pPSA and 100 ng/ml intact PSA was compared Development of Monoclonal Antibodies to BPSA Isoforms Processed, filtered seminal plasma was diluted 1:10 in PBS and passed over an immunoaffinity column with bound anti-PSA mAb, PSM773. The column was washed with 20 volumes of PBS containing 0.1% reduced Triton X100, and the PSA eluted with 100 mM glycine pH 2.5 containing 200 mM sodium chloride. The purified PSA was applied to HIC-HPLC as described previously [23] and the 8 min BPSA peak and the 10 min PSA peak were collected separately. The PSA from the 10 min peak was dialyzed into 100 mM Tris, pH 8 and incubated with 1% w/w trypsin for 30 min at 37 C. The trypsin in the mixture was inactivated by addition of a mass of aprotinin equal to twice the added trypsin. The incubation mixture was applied to HIC-HPLC and the resultant in vitro BPSA peak was collected. A detailed description of this process may also be found in the commonly owned co-pending U.S. patent application Ser. No. 09/303,208, the relevant content of which is incorporated herein by reference.

The in vitro BPSA was used as an immunogen in mice using standard protocols. Antibodies were selected on their ability to recognize the immunogen in preference to PSA which did not contain the clips at Lys 145 and Lys182. Using standard hybridoma technologies, the monoclonal antibody PS2E290, a BPSA specific mAb was developed. PS2E290 was used in a dual mAb immunoassay to detect BPSA in serum.

Immunoassay BPSA

The immunoassay we have developed for the measurement of BPSA is as follows. 50 ul of biotinylated anti-PSA Ab PSM 773 at 5 ug/ml in Tandem PSA zero cal diluent is added to a EG&G Wallac strep-avidin coated microplate and allowed to react at room temperature for 1 hour with shaking. The plate is then washed 5 times with Tandem E wash. 50 ul of Tandem PSA zero cal diluent is then added to the plate followed by 50 ul of sera or antigen to be tested. The mixture is allowed to react at room temperature for 2 hours as above. The plate is then washed 5 times with Tandem E wash. 100 ul of a 1 mA solution of PS2E 290—alkaline phosphatase conjugate is add to the plate. The mixture is allowed to react at room temperature for 1 hour as above. The plate is then washed 5 times with Tandem E wash. 100 ul of Sigma 4MU-p solution is added to each well and allowed to react at room temperature. After 1 hour the plate is read on a EG&G Wallac Victor instrument.

Amino Acid Sequencing of PSA

N-terminal sequence of the samples was performed through 9 cycles on a PE-Applied Biosystems Model 492 amino acid sequencer (PE-Applied Biosystems, Foster City, Calif.). Purified PSA and peaks collected by HIC-HPLC were applied directly to PVDF membranes using the Prosorb cartridges (PE-Applied Biosystems, Foster City, Calif.), washed 3× with 0.1 mL 0.1% trifluoroacetic acid, and applied to the Model 492 sequencer.

Example 1

Expression of pPSA in Mammalian Cells

The cDNA for PSA was cloned into the pGT-d vector under the control of the GBMT promoter using an approach similar to the one described for hK2 by Kumar et al. To study the expression of PSA, AV12 cells were transfected with the pGTD-PSA expression vector. Cells were selected in 400 nM methotrexate for 2-3 weeks, and single cell clones were analyzed for PSA expression using TANDEM®-MP PSA assay and on Western blots using mAb PSM 773. Clone AV12-PSA#8 was selected based on its high expression levels of a PSA-immunoreactive band at ~32 kDa.

Figure 2:
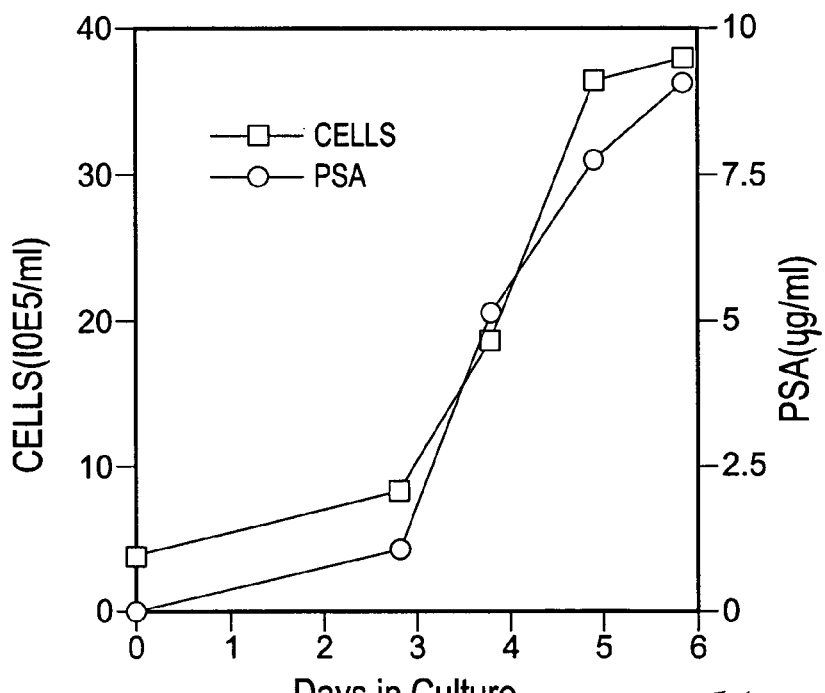
FIG. 2 depicts the expression of PSA by AV12-PSA#8 cells. Serum containing spent media of AV12-PSA#8 cells was harvested each day for 6sixconsecutive days. PSA concentration was measured using Tandem®-MP PSA assay. Viable cells were counted each day using trypan blue.

To determine the PSA expression pattern in mammalian cells, samples of spent media from AV12-PSA#8 cells were collected for six consecutive days and analyzed using the TANDEM®-MP PSA assay. FIG. 2 shows that PSA was detected in spent media at day 1 and accumulated to >9 μg/ml by day 6. Expression of PSA was higher during the log phase of cell growth, indicating that a stable form of PSA is secreted by the cells as opposed to being released following cell death and lysis. When the same samples were analyzed for free PSA, similar values were obtained (data not shown) indicating that AV12-PSA#8 cells express uncomplexed or free PSA.

Figure 3:
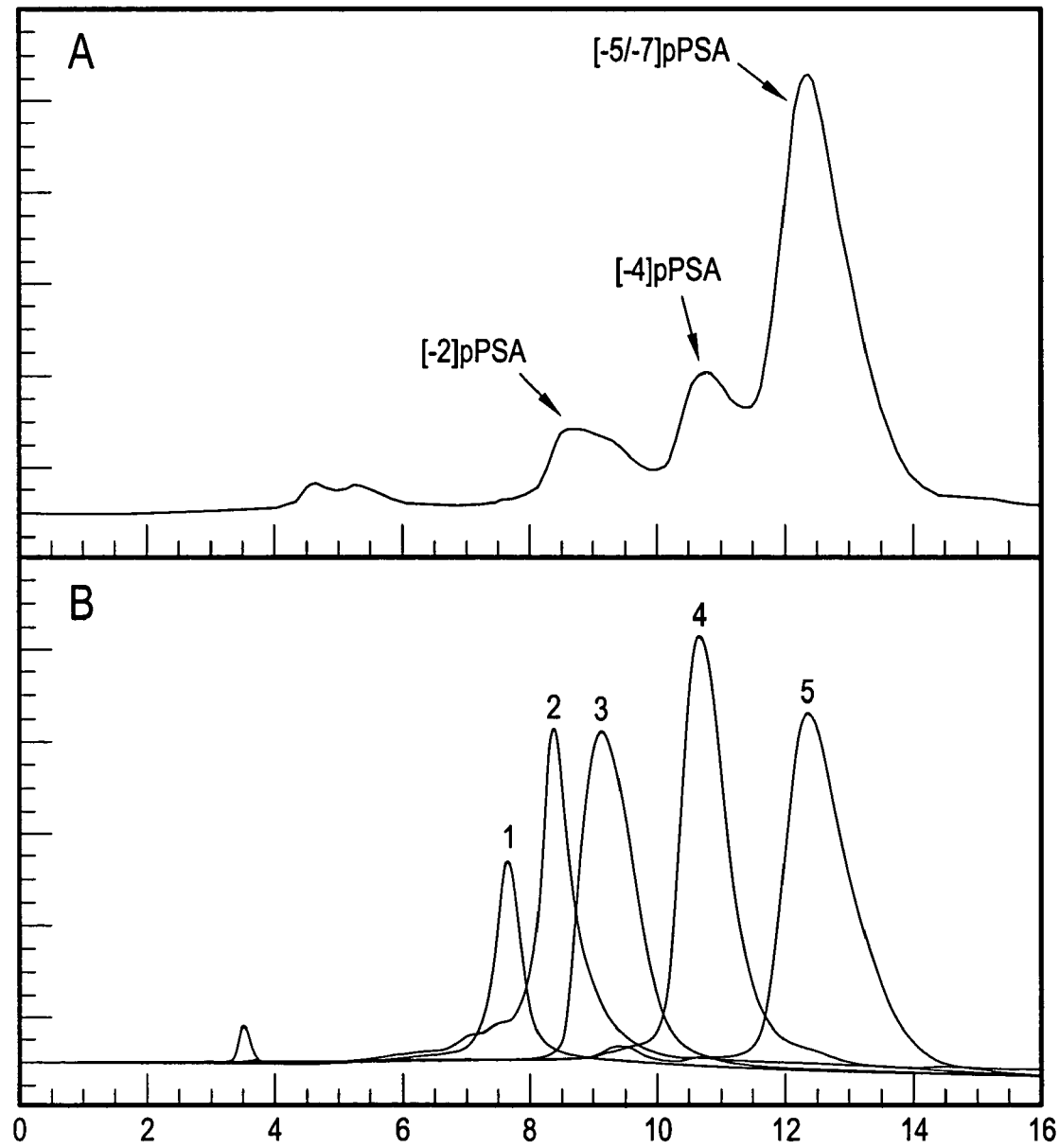
FIG. 3 shows chromatography profiles of different proteins. Panel A, hydrophobic interaction chromatography profile of the pPSA forms purified from the spent media of AV12 cells; and Panel B, relative elution profile of hK2, PSA, and pPSA forms.

To determine the identity of the protein that is secreted from the cells, the spent media from AV12-PSA#8 cells was collected and concentrated. The PSA in the media was purified by affinity chromatography using PSM 773, a PSA-specific mAb. The recombinant PSA expressed in mammalian AV12 cells was found to be secreted as pPSA as described previously in the commonly owned co-pending patent application Ser. Nos. 09/302,965, and 08/846,408. No measurable differences were observed between the PSA purified from day 1 or day 7 media. The pPSA was resolved into three different molecular forms by HIC-HPLC, as shown in FIG. 3A. PSA is normally expressed with a 7 aa pro leader peptide consisting of (SEQ ID NO:6) APLILSR but an N-terminal sequencing of the 3 peaks resolved by HIC-HPLC in FIG. 3A indicated truncated forms of pPSA. Peak A contained approximately equal levels of the 7 aa pro leader peptide (SEQ ID NO:6) APLILSR ([−7]pPSA) and a clipped, truncated 5 aa leader peptide containing (SEQ ID NO:7) LILSR ([−5]pPSA) that were not resolved from one another. Peak B contained the 4 aa pro leader peptide ILSR ([−4]pPSA). Peak C contained the 2 aa leader peptide, SR ([−2]pPSA), in addition to about 30% of PSA missing the first 4 aa of the mature sequence. Pure [−2]pPSA could be obtained by collecting the back half of this peak. The decrease in retention time of these proteins resulting from the incremental truncation of the pro leader peptide is most likely due to conformational changes in the pPSA protein and not due to the minor surface changes induced by removal of the indicated amino acids.

FIG. 3A shows that the different forms of pPSA can be resolved and purified form one another by HIC-HPLC. FIG. 3B is an overlay from several individual runs and shows the purified pPSA forms in addition to mature PSA and another prostate specific kallikrein, hK2. Thus, a single chromatographic run can separate and resolve all of the major forms of PSA protein from one another.

Example 2

Detection of pPSA in Pooled Human Prostate Cancer Serum

The presence of pPSA in human serum would indicate the following. First, that PSA is secreted as the pPSA form in human tissue and is converted to mature PSA extracellularly. Second, that pPSA is stable in human serum and thus may be a useful diagnostic marker for pCa or BPH. We evaluated the presence of pPSA in human serum by first using affinity purification to purify all forms of PSA present in a pool of human serum. We next fractionated the eluted PSA forms on HPLC and identified each PSA form based on its elution profile from the column. This analysis indicated that pPSA is present in human serum.

Figure 4A:
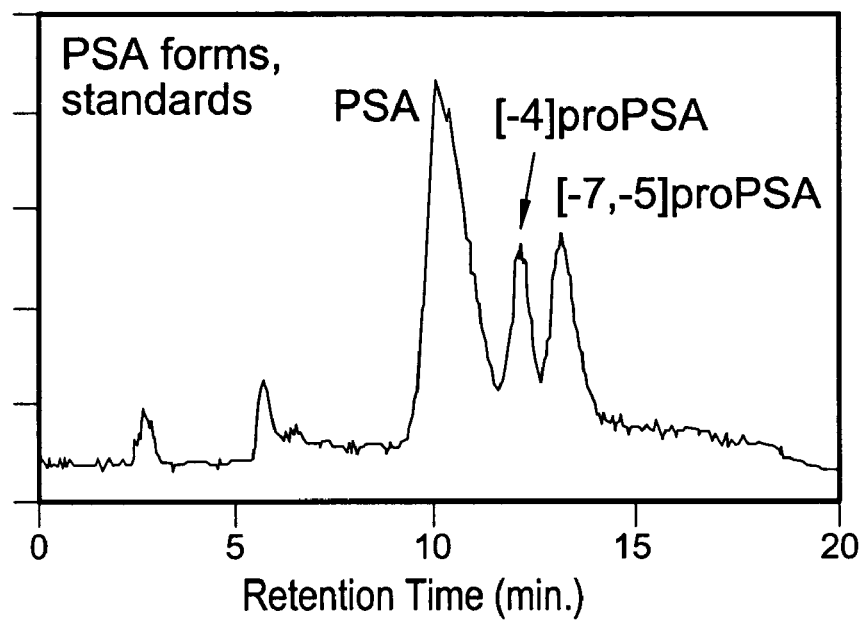
FIG. 4A shows the retention time for mature PSA and pPSA, including [−4]pPSA, [−5]pPSA and [−7]pPSA.
Figure 4B:
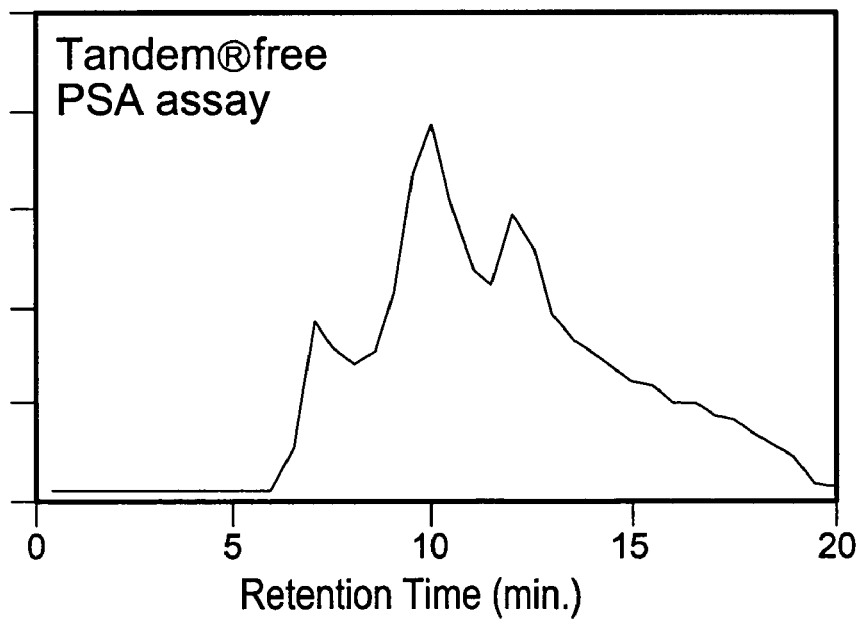
FIG. 4B shows the retention time for PSA forms from a serum sample bound to a PSM773 affinity column.

FIG. 4A shows the RT of standards of the different forms of PSA. All forms were verified by amino acid sequencing. The [−7, −5]pPSA peak contains approximately equal levels of [−7]pPSA and [−5]pPSA forms which are not resolved from each other. FIG. 4B shows the profile of PSA forms from serum bound to the PSM773 affinity column as described above. Samples were collected in 0.5 ml fractions and assayed by TANDEM®-MP free PSA assay (fPSA assay, Hybritech Incorporated). The fPSA assay detects both pPSA and free (inactive) PSA. The minor peak at seven minutes is due to the slight cross-reactivity of the fPSA assay to the PSA-ACT eluted from the affinity column. The actual level of PSA-ACT in this sample is about ten times higher than the level of free PSA (data not shown). The peaks at 10 minutes and 12 minutes correspond to mature PSA and [−4]pPSA, respectively. These data indicate that at least one form of pPSA ([−4]pPSA) is present in human serum and, as judged by the relative peak areas, it makes up approximately 25% of the free or uncomplexed PSA in this pooled serum sample.

Figure 5A:
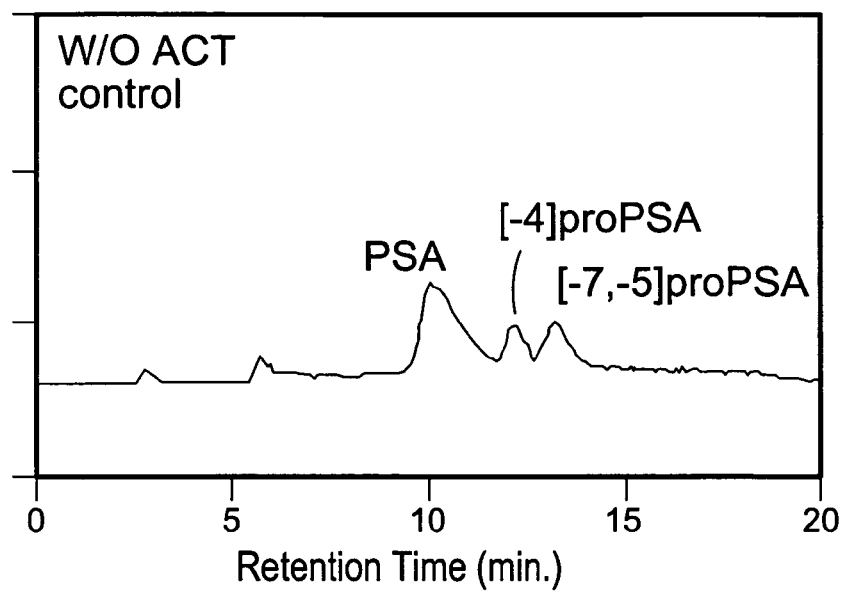
FIG. 5A shows the chromatographic profile for the protein mixture without the addition of ACT.
Figure 5B:
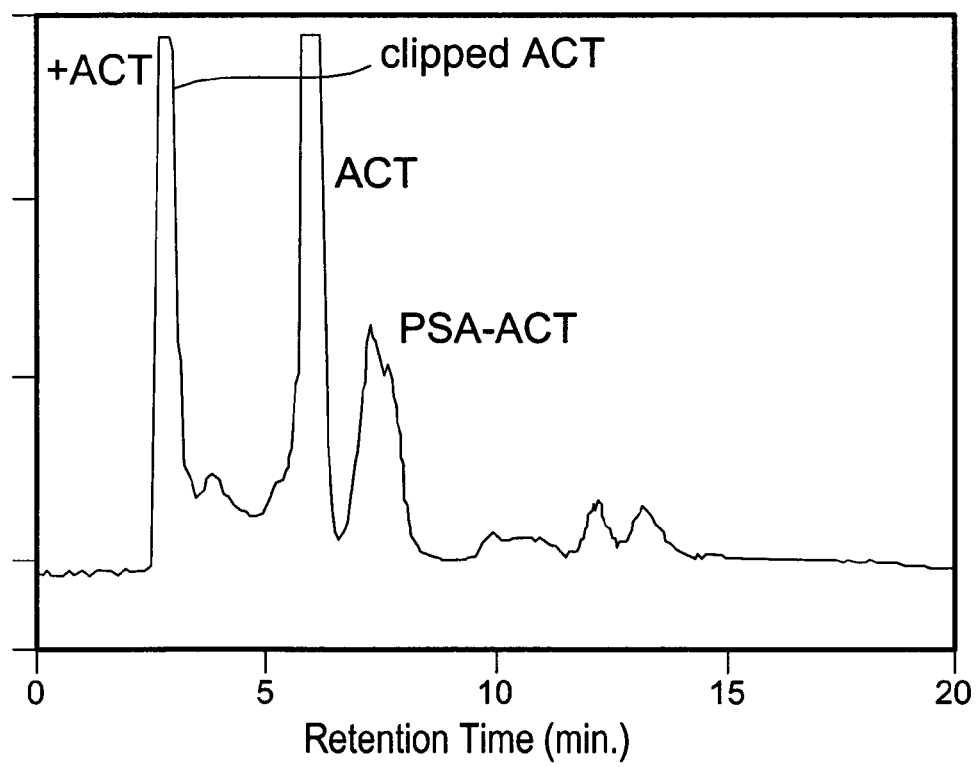
FIG. 5B shows the chromatographic profile for the same protein mixture after incubation with ACT for two hours at 37° C.

To confirm that the pro forms of PSA are not reactive with ACT, a mixture of purified mature PSA, [−4]pPSA and [−7, −5]pPSA, were incubated with ACT. FIG. 5A (W/O ACT) shows the chromatographic profile of the protein mixture without the addition of ACT. FIG. 5B (+ACT) shows the chromatographic profile of an identical amount of the same mixture after incubation with ACT for two hours at 37° C. Only the mature PSA forms an ACT complex. The [−4], [−5], and [−7] forms of pPSA did not form a complex with ACT, as they showed no decrease in peak area. This data is consistent with the [−4]pPSA in serum not being complexed with ACT.

Example 3

Detection of Truncated pPSA Forms in Prostate Cancer Serum

Figure 6:
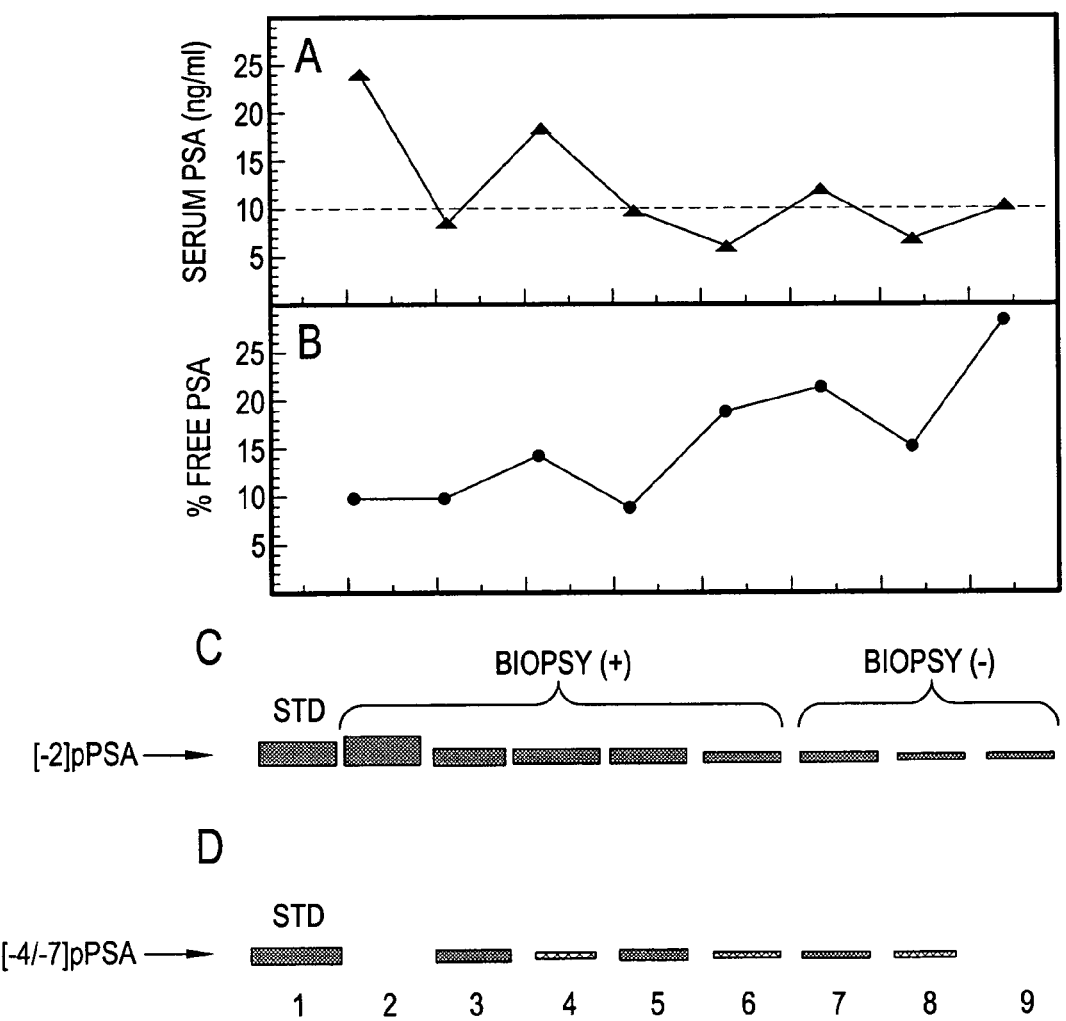
FIG. 6 are Western blots and immunoassay analyses of the PSA forms purified from the serum of prostate cancer biopsy-positive and biopsy-negative men: Panel A, total serum PSA prior to purification; Panel B, % free PSA in the serum prior to purification; Panel C, Western blot detection of [−2]pPSA; and Panel D, Western blot detection of [−4] plus [−7]pPSA.

Serum from several individual men were also analyzed by Western blot using newly devleoped pPSA mAbs. PSA was purified from the serum of men who were biopsy-positive and biopsy-negative for prostate cancer. The serum PSA values of the 5 biopsy-positive men were 6, 9, 10, 18, and 24 ng/ml. Three biopsy-negative men with 7, 10, and 12 ng/ml total PSA were also analyzed. Since the free PSA represented only 10-20% of the total PSA, and it was not known what percentage of the free PSA might be comprised of pPSA forms, it was necessary to purify PSA from 100-200 mls of serum in order to be assured of adequate detection sensitivity for Western blot analysis. Total PSA was purified from the serum by immunoaffinity chromatography using the anti-PSA mAb, PSM773, which recognizes all forms of free PSA and PSA bound to ACT. The recovery of PSA ranged from 30-60% of the amounts calculated to be in the starting serum by immunoassay. FIG. 6 shows the Western blot and immunoassay analysis of these samples. In panels A-D, all samples are shown in the same order. The first 5 samples were the PCa samples, and the last 3 samples were from biopsy-negative men. Panels A and B are the ng/ml of total PSA, and the % free PSA, respectively, in the serum prior to immunoaffinity purification. Panel B shows that the % free PSA was generally lower in the cancer samples compared to biopsy-negative or benign serum, which is in agreement with the predicted trend that BPH samples should contain higher % free PSA. It should be noted that the % free PSA measured in the purified PSA was unchanged from the original serum values, confirming that the purification procedure had no selectivity for either free or complexed forms of PSA.

Panels C and D are the Western blots of the same samples in panels A and B, probed with mAbs to [2]pPSA and [−4/−7]pPSA, respectively. In FIG. 6C, the blot was probed with PS2X373, which is specific for [−2]pPSA. Each lane was loaded with 1 ng of free PSA, as determined by prior immunoassay. Lane 1 contained 10 ng of purified [−2]pPSA standard. FIG. 6C shows that the 5 cancer samples contained the highest levels of [−2]pPSA. Comparing band intensity to the 10 ng [−2]pPSA standard in lane 1 indicates that nearly all of the free PSA in lane 2 is [−2]pPSA. [−2]pPSA was estimated to comprise about half of the free PSA in lanes 3-5, and to be 25% in lane 6 (Table 1). Lane 7, the first biopsy-negative sample, contained approximately 20% pPSA. The original serum assay for lane 7 measured 12 ng/ml total PSA, compared to 6 ng/ml in the cancer sample in lane 6 (panel A), though both contained comparable % free PSA (panel B). The biopsy-negative samples in lanes 8 and 9 contained only nominal levels of pPSA, perhaps 5-10%. Since the PS2X373 mAb had a minor cross-reactivity of approximately 5% with mature PSA under these Western blot conditions, it is possible that some or all of the apparent band in these lanes is due to PSA cross-reactivity.

In Panel D, 3 ng of free PSA was loaded in each lane and probed with PS2P446 which had equal specificity for [−4] pPSA and [−7]pPSA on Western blots. The results of this blot indicated that other forms of pPSA were present in only ⅔ of the cancer samples. PS2P446 had no cross-reactivity with mature PSA, and so the faint pPSA bands seen in ⅔ of the biopsy-negative samples indicated low levels of these pPSA forms. We had also developed mAbs with specificity for [−4]pPSA, and no cross-reactivity to other pro or mature forms of PSA, but these mAbs had a weak reactivity on blots, and consequently, a high background. While PS2V476 clearly indicated the presence of [−4]pPSA, quantification estimates were not possible. It is therefore not clear what proportion of the band intensities in panel D are due to [−4] pPSA or to full length [−7]pPSA. It is, however, evident that neither form of pPSA is as consistently present in the cancer serum as [−2]pPSA. In control experiments, female serum, passed over the immunoaffinity column and worked up identically with the male serum, showed no band of pPSA when probed with the above pPSA-specific mAbs.

Example 4

Immunohistochemical Staining of pPSA in Prostate Tissue

Figure 7:
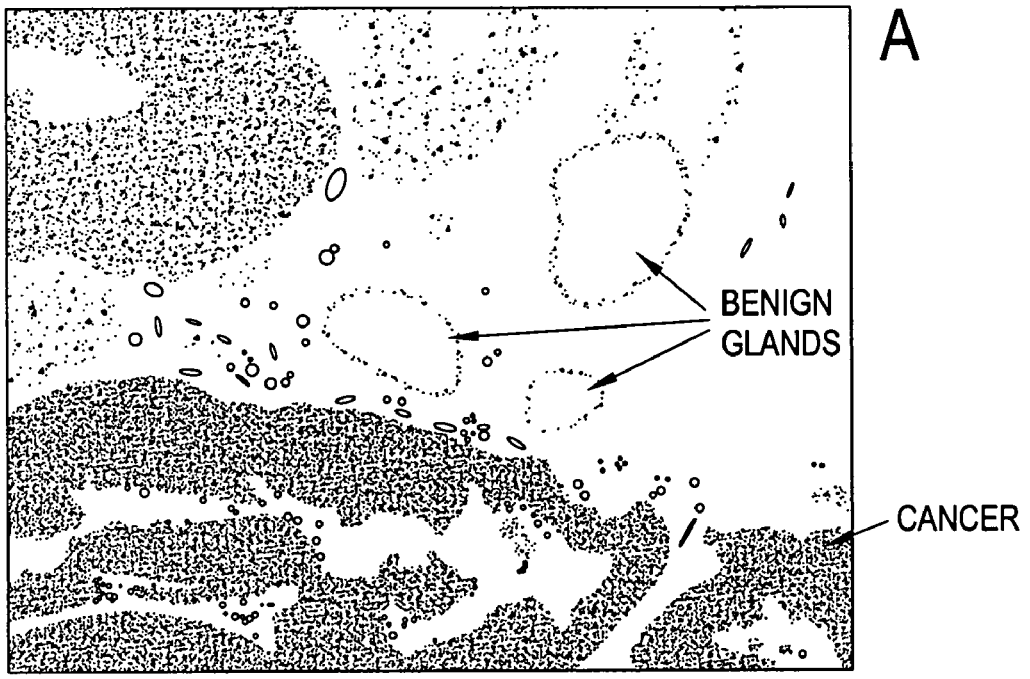
FIG. 7 shows the results of immunohistochemical staining of prostate tissues for [−2]pPSA.
Figure 7:

We tested the pPSA mAbs for staining on prostate tissues. The PS2P446 ([−7]/[−4]pPSA specificity) and PS2X373 ([−2]pPSA specificity) had similar staining intensities, while PS2V476 ([−4]pPSA specificity) did not work well for immunostaining. Both PS2X373 and PS2P446 showed a generally similar staining pattern as indicated in FIG. 7A, though PS2X373 showed more intense staining in cancer secretions as shown in FIG. 7B. Cancer epithelium showed consistent epithelial staining in the 9 cancers tested. PIN also showed consistent strong staining. Benign tissues stained less intensely than the cancer in general, though the surrounding benign tissues were more variable. FIG. 7A demonstrates that truncated pPSA forms can be detected in the epithelium of fixed prostate tissues, which provides further support that the truncated pPSA forms are not an artifactual result of tissue extraction, but are naturally present in prostate tissues. Since PS2X373 and PS2P446 recognize different forms of pPSA, comparable staining by both mAbs (not shown) indicates that multiple forms of pPSA are present in prostate tissues. The more intense staining of the [−2]pPSA in cancer secretions (FIG. 7B) could explain the prevalence of this form in the cancer serum.

Example 5

Immunoassay for BPSA in Human Serum

Figures 8, 9:
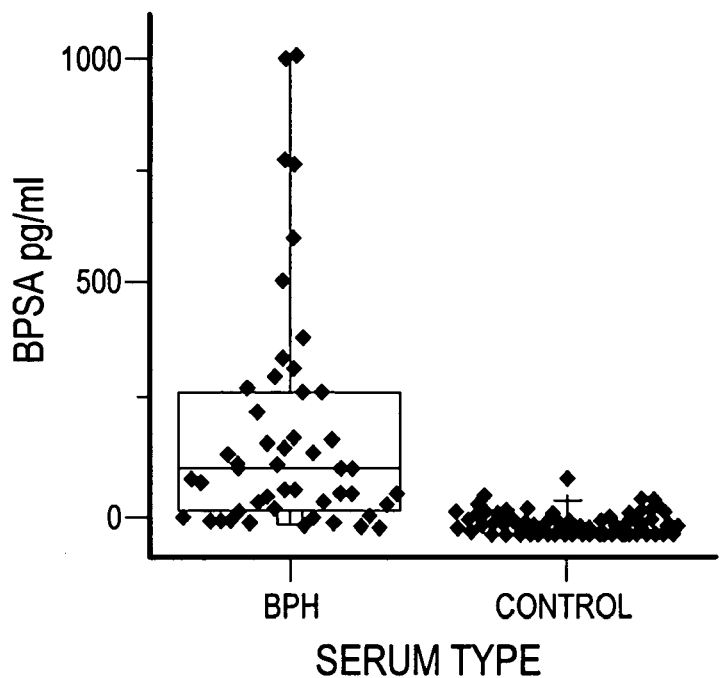
FIG. 8 is a dot plot that shows the immno-assay results of 52 men with clinical BPH and 92 controls.
FIG. 9 shows the ratio of [−2]pPSA/BPSA in biopsy-positive (i.e., cancer) and biopsy-negative samples contained essentially the same amount of total PSA in the serum.

We have previously identified a BPH-associated form of PSA called BPSA. A detailed description of this process may also be found in the commonly owned co-pending U.S. patent application Ser. No. 09/303,208, the relevant content of which is incorporated herein by reference. BPSA is found in prostate tissue containing BPH-nodules, but is not correlated with prostate cancer tissue. We have developed an immunoassay with high specificity and sensitivity for BPSA as described in the Methods section. Serum from 52 men diagnosed with clinical benign prostatic hyperplasia (BPH) were assayed for BPSA by immunoassay. In addition, 92 men with no diagnosis of prostate disease were also assayed for BPSA as a control group. FIG. 8 shows the assay results of 52 men with clinical BPH and 92 controls. Men with BPH contained a median BPSA level of 116 pg/ml, while the median BPSA level was below the minimum detectable limit of 60 pg/ml. These results demonstrate that BPSA is present in the serum of patients with clinically diagnosed BPH.

Example 6

The Ratio of [−2]pPSA and BPSA in Human Serum

The patient samples in FIG. 6 were further analyzed for BPSA by immunoassay. Table 1 shows the results of the [−2]pPSA and BPSA analysis. The [−2]pPSA values were determined by densitometric analysis of the Western blot bands, and BPSA was determined by immunoassay.

TABLE 1

| Lane #, FIG. 1 | % [−2]pPSA ([−2]pPSA/Free PSA) | % BPSA (BPSA/Free PSA) |
|---|---|---|
| 2 (cancer) | 95 | 7 |
| 3 (cancer) | 42 | 12 |
| 4 (cancer) | 49 | 16 |
| 5 (cancer) | 40 | 5 |
| 6 (cancer) | 25 | 14 |
| 7 (biopsy-negative) | 19 | 15 |
| 8 (biopsy-negative) | 6 | 13 |
| 9 (biopsy-negative) | 8 | 25 |

FIG. 9 shows 2 different examples of how the ratio of [−2]pPSA/BPSA could be used to detect prostate cancer. In each example the biopsy-positive (i.e., cancer) and biopsy-negative samples contained essentially the same amount of total PSA in the serum. In example A, both samples contained about 10 ng/ml total PSA. The cancer sample contained high [−2]pPSA and low BPSA compared to the PSA-matched biopsy-negative sample. This results in a [−2]pPSA/BPSA ratio for the cancer serum that is 25-fold higher than the biopsy-negative serum.

The serum samples in example B contained about 6 ng/ml PSA. This PSA value is in the diagnostic "gray zone" of 4-10 ng/ml where it is very difficult to distinguish prostate cancer from benign disease. While both samples contain comparable levels of BPSA, the [−2]pPSA was significantly elevated in the cancer serum. In this case the [−2]pPSA/BPSA ratio of the cancer serum was 4-fold higher than the biopsy-negative serum, and provides a clear correlation with prostate cancer.

Example 7

[−2]pPSA is a stable, Inactive Form of pPSA

We have previously shown that hK2 and trypsin can activate [−5/−7]pPSA to mature PSA (see the commonly owned co-pending patent application Ser. Nos. 09/302,965, and 08/846,408). In the current study, we tested the [−4] and [−2]pPSA forms in order to determine if these isoforms had altered susceptibility to activation. hK2 was incubated with each of the pPSA forms and the proportion of each form was monitored by HIC-HPLC as shown in FIG. 3B.

Figure 10:
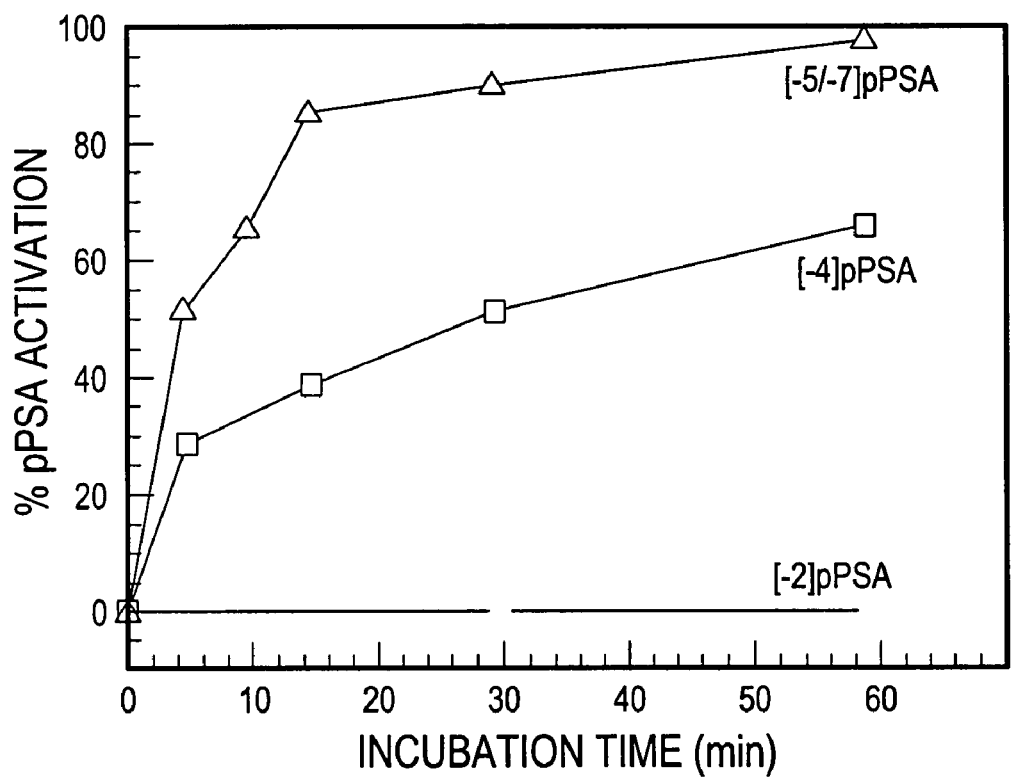
FIG. 10 shows the relative activation rates of [−2]pPSA, [−4]pPSA, and [−5/−7]pPSA by hK2.
Figure 11:
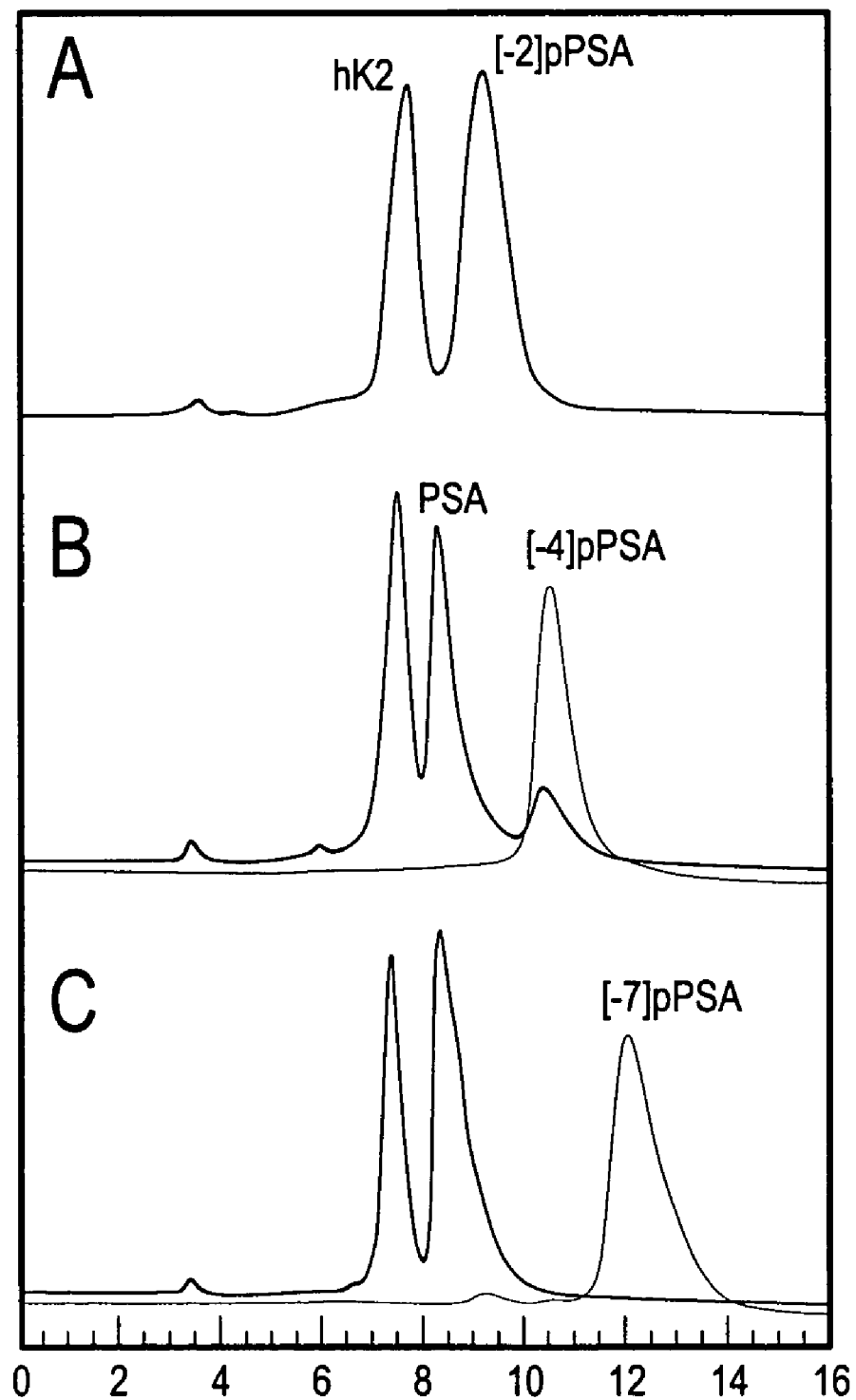
FIG. 11 is a hydrophobic interaction chromatographic profile showing that [−2]pPSA was not activated to PSA after 5 h incubation with hK2 (panel A). The [−4]pPSA (panel B) and [−5/−7]pPSA were converted to PSA.

FIG. 10 shows the relative rate of pPSA activation by hK2. The [5/−7]pPSA was activated most rapidly, while the [−4] pPSA was activated more slowly. Most significantly, [−2] pPSA was not activated by hK2. FIG. 11 shows the chromatographic profile of pPSA forms after an extended incubation of 40% hK2 with the individual isoform of pPSA. After 5 h of incubation at 37° C., [−2]pPSA still showed no evidence of conversion to mature PSA (FIG. 11A). After incubation for 2 h, the majority of the [−4]pPSA was converted (FIG. 11B). By contrast, the [−5] and [−7]pPSA forms were converted to mature PSA in less than an hour (FIG. 11C). It should be noted that the ratio of the [−5] and [−7]pPSA species contained within the 12 min peak in panel C was unchanged throughout the activation process, as determined by N-terminal sequencing, indicating that these two species were biochemically indistinguishable as substrates for hK2. Therefore, the major shift in HIC-HPLC retention time and in the activation kinetics of pPSA forms occurred upon removal of the single additional [−5] leucine residue. These differences between the [−5] and the [−4]pPSA forms suggests that the [−5] leucine plays an important role in the folding of pPSA.

In addition to hK2, we have previously shown that 1% trypsin rapidly activates pPSA in 15 min. We therefore tested trypsin for its ability to activate [−2]pPSA, since trypsin is a far more active protease than hK2, has a strong specificity for arginine (and lysine) residues, and is little affected in its hydrolytic activity by amino acids adjacent to the P1 cleavage site, other than proline. After an extended incubation with trypsin, other internal arginine/lysine sites were cleaved (as determined by N-terminal sequencing), but there was little or no cleavage to release the SR dipeptide of the [−2]pPSA (data not shown).

Thus, the pro leader dipeptide on [−2]pPSA appears to be resistant to cleavage by proteases that are otherwise capable of cleaving the [−4] and [−5/−7] pro leader peptides.

In an experiment similar to that shown in FIG. 5, none of the pPSA isoforms formed a complex with a 4x excess of ACT after 5 h of incubation at 37° C. (data not shown). This demonstrated that all truncated and full-length pPSA forms were enzymatically inactive and would thus be expected to remain as free PSA in serum.

Example 8

Monoclonal Antibodies with Preferential Reactivity to ProPSA

Using the methods described, the following antibodies were generated in PS1Z fusion: PS1Z134, PS1Z120, PS1Z125 and PS1Z81. Table 1 shows the results of screening at initial testing (proPSA alone), retest and expansion phases (comparison of proPSA response to PSA response). These monoclonal antibodies demonstrated elevated response to proPSA (approximately 2 fold) over response to PSA. This ability to differentiate proPSA from PSA was maintained when the clones were grown in large size culture condition.

TABLE 2

Specificity analysis of proPSA reactive hybridomas.

| | Assay Response (A490) to proPSA vs PSA | | Cell Expansion |
|---|---|---|---|
| Clone | Initial screening ProPSA | Retest proPSA to PSA ratio | proPSA to PSA ratio |
| PS1Z134 | + | 2.3 | 2.0 |
| PS1Z120 | + | 2.0 | 1.49 |
| PS1Z125 | + | 2.2 | 1.58 |
| PS1Z81 | + | 2.0 | 1.35 |

Example 9

Characterization of pPSA Monoclonal Antibodies Specific for pPSA

Figure 12:
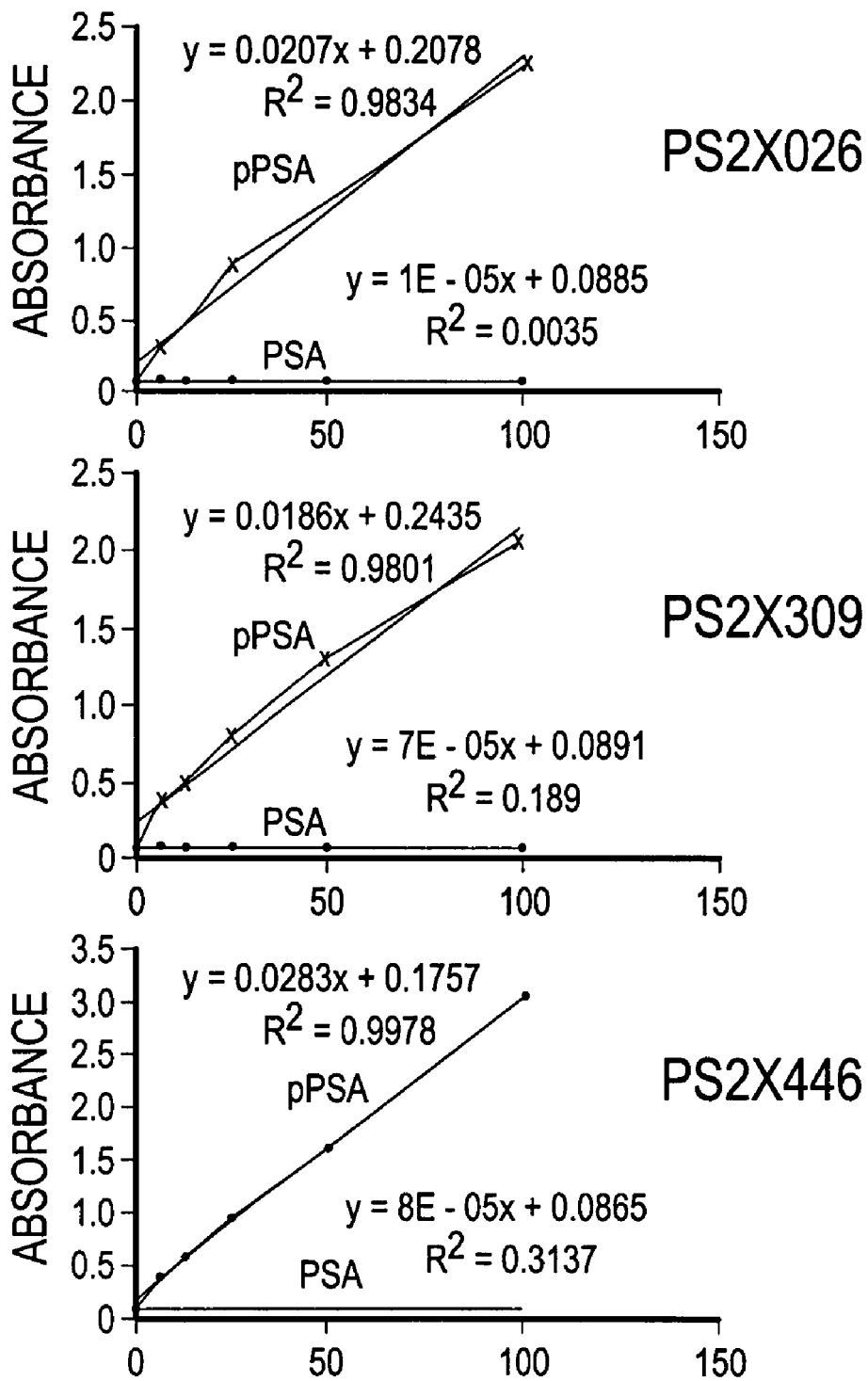
FIG. 12 shows the results of immunoassay analysis of 3 different pPSA mAbs showing a high specificity for [−7] pPSA and no significant specificity for mature PSA.

Monoclonal antibodies (mAbs) were prepared against full length [−7]pPSA by immunization with the chimeric recombinant protein consisting of hK2 with the (SEQ ID NO:6) APLILSR pro PSA leader peptide. Since the first 17 N-terminal amino acids of hK2 are identical to PSA, the substitution of the pPSA pro leader peptide onto hK2 provides advantages in the immunization and screening procedures with pPSA since antibodies to the remainder of the mature PSA protein are not induced. FIG. 12 shows the sandwich immunoassay showing that 3 mAbs, PS2P206, PS2P309 and PS2P446, have a high specificity for pPSA compared to the mature form of PSA.

Figure 13:
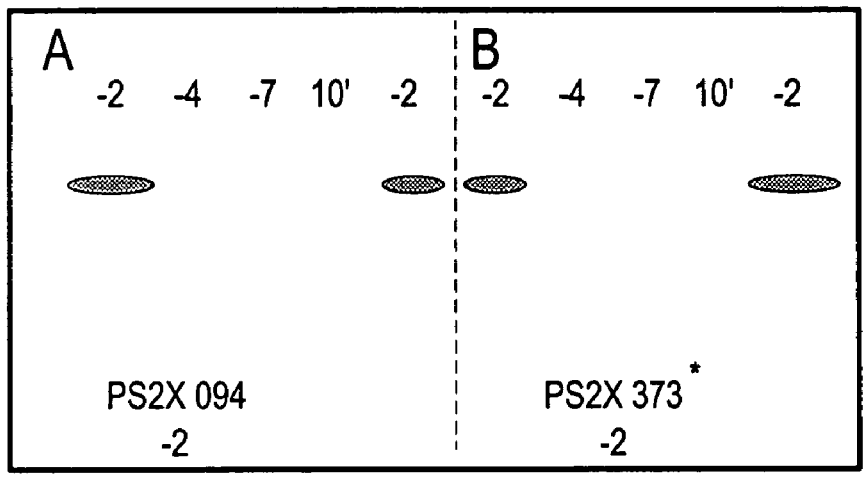
FIG. 13 are Western blots of different mature and pro PSA forms probed with different mAbs that demonstrates specificity for [−2], [−4] and [−7]pPSA.
Figure 13:
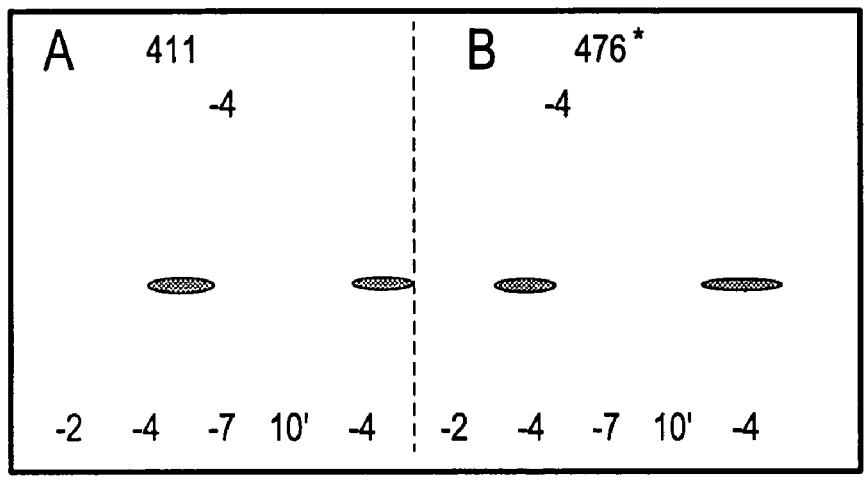
Figure 13:
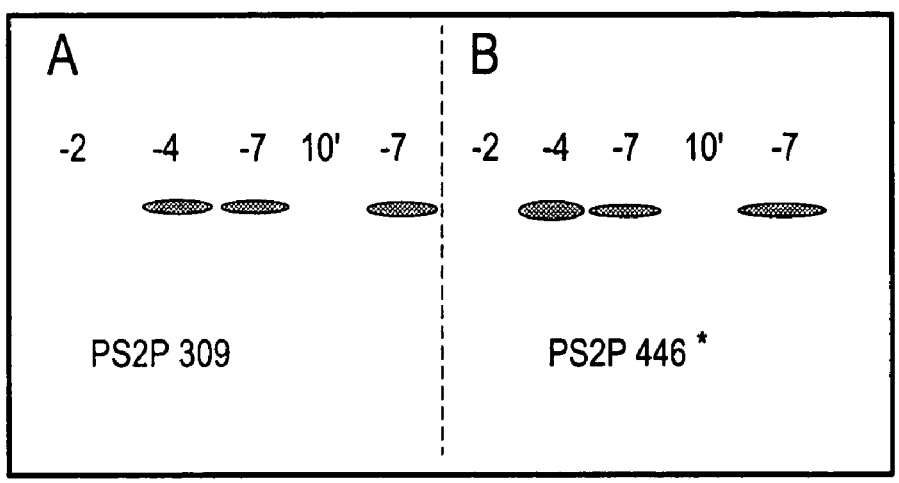

In addition to the above, mAbs to the truncated forms of pPSA, specifically [−2]pPSA and [−4]pPSA were obtained by immunization with peptides consisting of (SEQ ID NO:3) SRIVGGWECEK, and (SEQ ID NO:4) ILSRIVGGWECEK, respectively. FIG. 13, the top and middle panels, shows the specificity of 2 mAbs each. Each blot was cut in half, indicated by the dotted line, and probed with 2 different mAbs (A and B). In the top panel, the 2 [−2]pPSA mAbs, PS2X094, and PS2X373, are shown. The lanes designated −2 indicates [−2]pPSA; −4, [−4]pPSA; −7, [−7]pPSA; and 10' indicates mature PSA. Each lane was loaded with 100 .mu.g of protein. The blot shows that each of the [−2]pPSA mAbs has high specificity for [−2]pPSA and negligible reactivity with the [−4]pPSA, [−7]pPSA, and mature PSA. In other experiments, these mAbs showed a cross-reactivity of about 20% for mature PSA when the gels were run under reducing conditions, and about 5% when the gels were run under non-reducing conditions. The middle panel shows identical blots probed with 2 [−4]pPSA mAbs, PS2V411, and PS2V476. These mAbs show only minimal cross-reactivity to [−2]pPSA and no cross-reactivity to [−7]pPSA or mature PSA. The bottom panel in FIG. 13 shows an identical blot probed with 2 [−7]pPSA nAbs, PS2P309, and PS2P446. These are two of the mAbs described in FIG. 12. This blot shows that under denaturing conditions on a Western blot, these mAbs have equivalent reactivities with the [−4] and [−7]pPSA forms, but no reactivity to [−2]pPSA and mature PSA.

Figure 14:
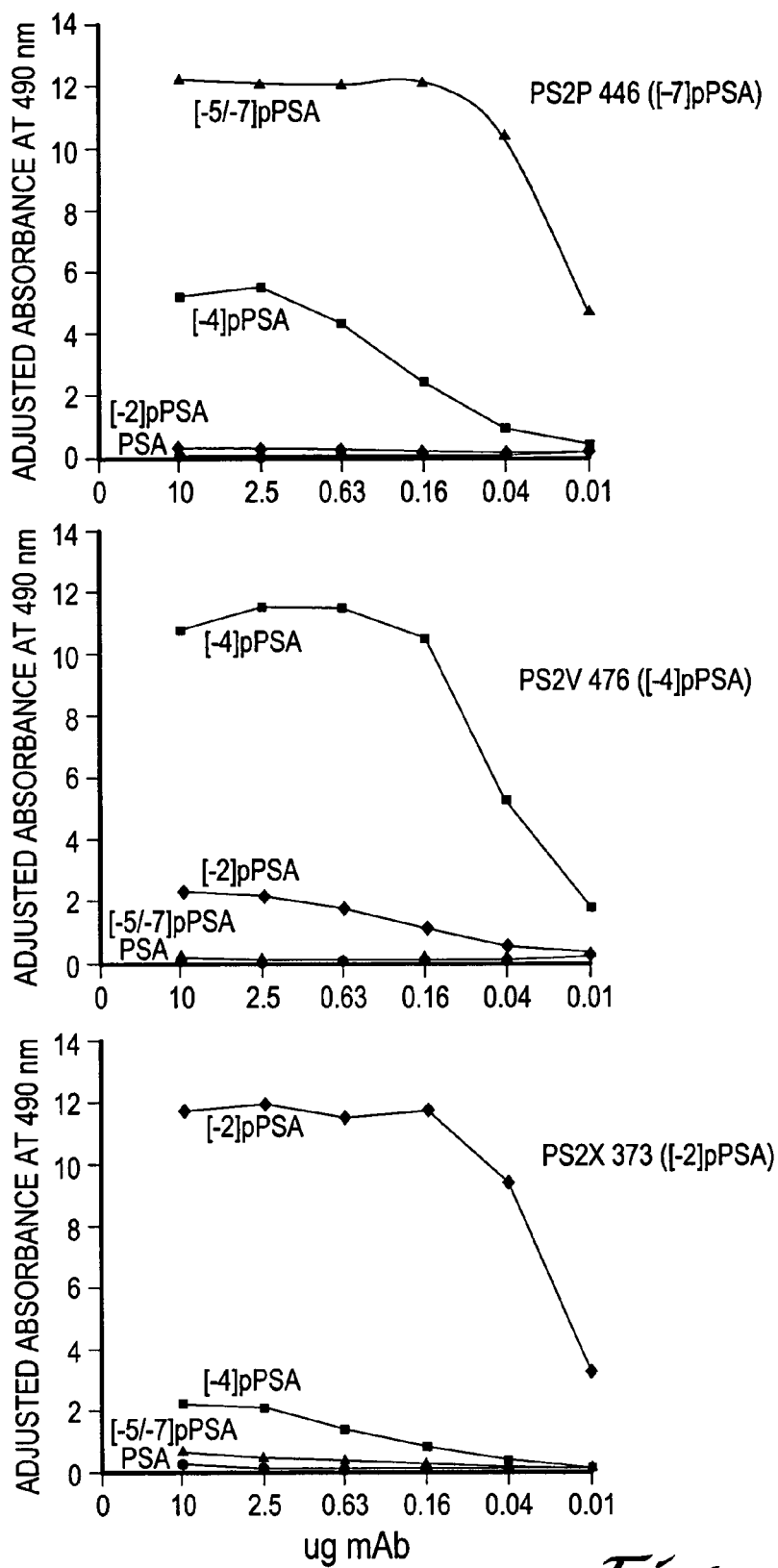
FIG. 14 shows an immunoassay of 3 different mAbs, PS2X373, PS2V276 and PS2P446, showing their relative reactivities towards [−2]pPSA, [−4]pPSA, [−4/−7]pPSA and mature PSA.

The three mAbs with selective pPSA specificities, PS2P446 ([−7]/[−4]pPSA specificity), PS2V476 ([−4]pPSA specificity), and PS2X373 ([−2]pPSA specificity), were also tested on their relative reactivities to each other, and to mature PSA in a sandwich assay, microtiter plate. In this case, the biotinylated Fab' of mAb PS2J163 which binds to all PSA forms [24] was bound to a streptavidin-coated microtiter plate, and incubated with the indicated form of pPSA as seen in FIG. 14. The above 3 mAbs were then serially diluted and incubated with the different bound PSA and pPSA antigens. The binding of the pPSA mAbs was detected with anti-mouse-HRP antibodies. FIG. 14 shows that each of the pPSA mabs had specificity for their indicated form of pPSA. There is some cross-reactivity to other pPSA forms in some cases, but all show negligible reactivity to mature PSA. The important result of this experiment is that it shows that mAbs raised to both pPSA proteins and peptides are capable of reacting with good specificity to the appropriate native pPSA under conditions suitable for the development of an immunoassay.

DISCUSSION

The present invention has employed several novel approaches that have resulted in the development of mAbs to detect and discriminate between 3 different isoforms of pPSA (FIGS. 12-14). These mAbs contained the required properties of high sensitivity and specificity to the different pPSA forms compared to mature PSA.

Using these mAbs, we were able to determine that different pPSA forms exist in serum, and that the [−2] appears to be the most prevalent form (FIG. 6). Just as importantly, it was found that [−2]pPSA comprised a significant percentage of the free PSA in prostate cancer serum, ranging from 25-95% of the free PSA (Table 1). Of equal importance, this occurred in the serum of men with total PSA values from 6-24 ng/ml. Thus, [−2]pPSA represents a significant and relevant isoform of PSA for the study of prostate cancer. It is in the range below 10 ng/ml that it is most difficult to discriminate PCa from benign conditions such as BPH since both conditions release PSA into the Serum[13,25]. Repeat biopsies are often performed in biopsy-negative men with elevated PSA levels. This is because a positive biopsy is conclusive proof of prostate cancer, while a negative biopsy may simply have missed the areas of cancer[26]. For this reason the measurement of pPSA forms may offer additional diagnostic value.

In our study using pooled cancer serum containing 63 ng/ml total PSA, we identified the truncated [−4]pPSA using HIC-HPLC (FIG. 4). In a more detailed study using pPSA mAbs and individual patient serum we have shown that [−2] pPSA may be the more predominant form (FIG. 6). There is, however, no conflict with these results since, in FIG. 4, we used chromatographic methodologies to identify the different forms of PSA. The HIC-HPLC approach required that elution fractions be collected and the PSA measured by immunoassay. Because PSA and [−2]pPSA elute closely (see FIG. 3B), it was not possible to distinguish these 2 isoforms of PSA in the FIG. 4 due to the loss of peak resolution incurred by fraction collection. Therefore, only the [−4]pPSA form was clearly resolved from the PSA peak. It is not known, but it is likely, that the PSA peak in FIG. 4B contained some percentage of [−2]pPSA.

The reason for the enrichment of a stable, truncated form of pPSA in tissues and, ultimately, serum was suggested by the activation studies. It has been previously demonstrated that pPSA can be activated by hK2 and trypsin[22,27,28]. Since hK2 and PSA are co-localized in the prostate columnar epithelial cells[29], it has been speculated that hK2 may be the endogenous protein responsible for the activation of PSA. The process of pPSA activation is normally an extremely efficient process since pPSA forms are undetectable in seminal plasma (data not shown). FIG. 10 shows that hK2 has no ability to activate [−2]pPSA and has reduced activity on [−4]pPSA compared to [−5/−7]pPSA. Even trypsin, which has a much wider substrate specificity range and activates pPSA at least 10× more rapidly than hK2, was unable to activate [−2]pPSA (data not shown). An extended incubation with trypsin resulted in cleavage at other internal sites in PSA, without significant cleavage of the serine-arginine pro leader peptide. While there is no direct evidence that hK2 is responsible for the activation of pPSA the failure of both hK2 and trypsin to activate [−2]pPSA makes it less likely that [−2]pPSA remains a viable substrate for other activation proteases.

The present invention is the first description of the relative levels of different pPSA forms in serum, and is in direct contrast to other reports in the literature that were unable to detect pPSA by other techniques[9,10], or were unable to develop the mAbs necessary to attempt pPSA detection in serum[12].

While not wanting to be bound by the theory, it is possible that the truncation of pPSA to [−2]pPSA is the result of post-translational proteolytic cleavage. In our study of tissue extracts, we found that [−2]pPSA was the most elevated in cancer[30]. In the transition zone, the site of BPH, the median value of [−2]pPSA dropped to 0. This is important, since PSA leaks into the serum as the result of cancer and BPH. Since [−2]pPSA was not present in BPH transition zone tissue, it follows that [−2]pPSA in the serum came from cancer tissues or surrounding peripheral zone tissue. The immunostaining of prostate tissues (FIG. 7) adds important insight to our tissue extract results by confirming the strong association of pPSA forms with cancerous epithelium. The results in FIG. 6 support this hypothesis by showing strongly elevated levels of [−2]pPSA in PCa serum. In contrast, PSA released from the transition zone due to BPH would be expected to contain little or no [−2]pPSA. While 5/5 cancer sera contained significant levels of [−2]pPSA, ⅔ biopsy negative, i.e., potential BPH serum, contained only trace levels of [−2]pPSA.

Since elevated levels of free PSA have been shown to better correlate with a benign disease[14,25,31], it may seem counter intuitive that cancer serum contains elevated levels of pPSA forms, which are also found as free PSA. However, FIG. 6 shows that pPSA represents a minor percentage of the free PSA in benign disease and a major percentage in cancer. The cancer samples had a lower % free PSA than the benign samples, but a much higher relative percentage of the free PSA was [−2]pPSA. As the % free PSA increased in the biopsy-negative samples, it was apparently comprised of increasing amounts of inactive PSA forms other than [−2] pPSA. Thus, pPSA makes up a progressively smaller percentage of the % free PSA that derives from a benign disease. Since men with prostate cancer can also develop BPH and vice versa, it will be important to determine the relative contribution of pPSA in each disease state.

[−2]pPSA, or other pPSA forms, could offer the greatest diagnostic value as the percentage of total PSA, as a percentage of the free PSA, or as an independent indicator where pPSA levels above a certain threshold have a high statistical correlation with cancer. In the latter case, it is conceivable that the presence of pPSA could offer diagnostic value in serum containing any measurable level of pPSA, and especially in serum with less than 4 ng/ml total PSA.

We have recently developed an immunoassay to detect serum BPSA, the BPH associated form of PSA. A pPSA immunoassay in combination with an assay for BPSA may add even greater discrimination of PCa from BPH. The results of the present invention show that proPSA, such as [−2]pPSA, is elevated in prostate cancer serum (FIG. 6) and that BPSA is elevated in BPH serum (FIG. 8). In 2 examples of biopsy-positive and biopsy-negative serum with matched total PSA, the ratio of [−2]pPSA/BPSA showed a clear differential between cancer and benign disease (FIG. 9).

It is interesting to note that the [−2]pPSA/BPSA ratio showed a significantly better differential between cancer and benign disease than the analysis of free and total PSA (an analysis currently used to distinguish prostate cancer from BPH). In FIG. 9, Example A, each sample contained total PSA near 10 ng/ml, but very different percentages of % Free PSA. The cancer serum contained 9% Free PSA, while the biopsy-negative serum contained 28% Free PSA. In numerous studies, %Free PSA values less than 10% are more highly correlated with cancer, while values greater than 25% have a low correlation with cancer. For the samples in Example A the ratio of [−2]pPSA/BPSA was 25-fold higher in the cancer serum compared to the biopsy-negative serum.

FIG. 9, Example B shows serum samples that are more difficult to interpret with the conventional free and total PSA assays. The total PSA is in the diagnostic "gray zone" of 4-10 ng/ml, and both samples also contained %Free PSA in the diagnostic %Free PSA "gray zone" between 10% and 25%. With current assay protocols employing only free and total PSA there is no clear differential and no clear indication of prostate cancer in either sample. However, the [−2]pPSA was elevated in the cancer sample, and the [−2]pPSA/BPSA ratio was still 4-fold higher in the cancer sample.

These examples indicate that the analysis of the [−2]pPSA and BPSA isoforms of PSA, and the ratio thereof, may add significantly to the detection of prostate cancer.

The invention may be embodied in other specific forms without departing from its essential characteristics. The described embodiments are to be considered in all respects only as illustrative and not as restrictive. Indeed, those skilled in the art can readily envision and produce further embodiments, based on the teachings herein, without undue experimentation. The scope of the invention is, therefore, indicated by the appended claims rather than by the foregoing description. All changes that come within the meaning and range of the equivalence of the claims are to be embraced within their scope.

REFERENCES LIST

1. Catalona, W. J., Smith, D. S., Ratliff, T. L., Dodds, K. M., Coplen, D. E., Yuan, J. J., Tetros, J. A., and Andriole, G. L. Measurement of prostate-specific antigen in serum as a screening test for prostate cancer. N Engl J Med, 324: 1156-1161, 1991.
2. Oesterling, J. E. Prostate-specific antigen: a critical assessment of the most useful tumor marker for adenocarcinoma of the prostate. J Urol, 145: 907-923, 1991.
3. Labrie, F., Dupont, A., Suburu, R., Cusan, L., Tremblay, M., Gomez, J. L., and Emond, J. Serum prostate specific antigen as pre-screening test for prostate cancer. J Urol, 147: 846-851, 1992.
4. Lilja, H., Christensson, A., Dahlen, U., Matikainen, M. T., Nilsson, O., Pettersson, K., and Lovgren, T. Prostate-Specific Antigen in Serum Occurs Predominantly in Complex with $\alpha_1$-antichymotrypsin. Clin Chem, 37: 1618-1625, 1991.
5. Stenman, U. H., Leinonen, J., Alfthan, H., Rannikko, S., Tuhkanen, K., and Alfthan, O. A complex between prostate specific antigen and $\alpha_1$-antichymotrypsin is the major form of prostate-specific antigen in serum of patients with prostatic cancer: assay of the complex improves clinical sensitivity for cancer. Cancer Res., 51: 222-226, 1991.
6. Catalona, W. J., Partin, A. W., Slawin, K. M., Brawer, M. K., Flanigan, R. C., Patel, A., Richie, J. P., deKernion, J. B., Walsh, P. C., Scardino, P. T., Lange, P. H., Subong, E. N., Parson, R. E., Gasior, G. H., Loveland, K. G., and Southwick, P. C. Use of the percentage of free prostate-specific antigen to enhance differentiation of prostate cancer from benign prostatic disease: a prospective multicenter clinical trial. Jama, 279: 1542-1547, 1998.
7. Woodrum, D. L., Brawer, M. K., Partin, A. W., Catalona, W. J., and Southwick, P. C. Interpretation of free prostate specific antigen clinical research studies for the detection of prostate cancer. J Urol, 159: 5-12, 1998.
8. Peter, J., Unverzagt, C., and Hoesel, W. Analysis of free prostate-specific antigen (PSA) after chemical release from the complex with alpha(1)-antichymotrypsin (PSA-ACT). Clin.Chem., 46: 474-482, 2000.
9. Noldus, J., Chen, Z., and Stamey, T. Isolation and characterization of free form prostate specific antigen (f-PSA) in sera of men with prostate cancer. J Urol., 158: 1606-1609, 1997.
10. Hilz, H., Noldus, J., Hammerer, P., Buck, F., Luck, M., and Huland, H. Molecular heterogeneity of free PSA in sera of patients with benign and malignant prostate tumors [In Process Citation]. Eur Urol, 36: 286-292, 1999.
11. Paus, E., Nustad, K., and Bormer, O. P. Epitope mapping and affinity estimation of 83 antibodies against prostate-specific antigen. Tumour.Biol., 20 *Suppl* 1: 52-69, 1999.
12. Nurmikko, P., Vaisanen, V., Piironen, T., Lindgren, S., Lilja, H., and Pettersson, K. Production and characterization of novel anti-prostate-specific antigen (PSA) monoclonal antibodies that Do not detect internally cleaved Lys145-Lys146 inactive PSA [In Process Citation]. Clin.Chem., 46: 1610-1618, 2000.
13. Catalona, W. J., Smith, D. S., Ratliff, T. L., Dodds, K. M., Coplen, D. E., Yuan, J. J., Tetros, J. A., and Andriole, G. L. Measurement of prostate-specific antigen in serum as a screening test for prostate cancer. N Engl J Med, 324: 1156-1161, 1991.
14. Woodrum, D. L., Brawer, M. K., Partin, A. W., Catalona, W. J., and Southwick, P. C. Interpretation of free prostate specific antigen clinical research studies for the detection of prostate cancer. J Urol, 159: 5-12, 1998.
15. Berg, D. T., McClure, D. B., and Grinnell, B. W. E1a-responsive mammalian host/vector system for the stable high-level expression of secreted proteins. Nucleic Acids Res., 20: 5485-5486, 1992.
16. Wang, T. J., Linton, H. J., Sokoloff, R. L., Grauer, L. S., Rittenhouse, H. G., and Wolfert, R. L. Antibody specificities for PSA and PSA fragments by SDS-PAGE Western blot analysis. Tumor Biology, 20: 75-78, 1997.
17. Finlay, J. A., Day, J. R., and Rittenhouse, H. G. Polyclonal and Monoclonal Antibodies to Prostate-Specific Antigen can Cross-React with Human Kallikrein 2 and Human Kallikrein 1. Urology, 53: 746-751, 1999.
18. Kumar, A., Mikolajczyk, S. D., Goel, A. S., Millar, L. S., and Saedi, M. S. Expression of pro form of Prostate-specific antigen by mammalian cells and its conversion to mature, active form by human kallikrein 2. Cancer Res, 57: 3111-3114, 1997.
19. Christensson, A., Laurell, C. B., and Lilja, H. Enzymatic activity of prostate-specific antigen and its reactions with extracellular serine proteinase inhibitors. Eur J Biochem, 194: 755-763, 1990.
20. Knott, C. L., Kuus-Reichel, K., Liu, R. S., and Wolfert, R. L. Development of antibodies for diagnostic assays. In: *Principles and Practice of Immunoassay*. Price, C. P. and Newman, D. J. 37-64.1997. New York, NY, Stockton Press. Ref Type: Serial (Book,Monograph)
21. Kumar, A., Goel, A., Hill, T., Mikolajczyk, S., Millar, L., Kuus-Reichel, K., and Saedi, M. Expression of human glandular kallikrein, hK2, in mammalian cells. Cancer Res., 56: 5397-5402, 1996.
22. Kumar, A., Mikolajczyk, S. D., Goel, A. S., Millar, L. S., and Saedi, M. S. Expression of pro form of Prostate-specific antigen by mammalian cells and its conversion to mature, active form by human kallikrein 2. Cancer Res, 57: 3111-3114, 1997.
23. Mikolajczyk, S. D., Millar, L. S., Wang, T. J., Rittenhouse, H. G., Wolfert, R. L., Marks, L. S., Song, W., Wheeler, T. M., and Slawin, K. M. "BPSA," a specific molecular form of free prostate-specific antigen, is found predominantly in the transition zone of patients with nodular benign prostatic hyperplasia. Urology, 55: 41-45, 2000.
24. Wang, T. J., Slawin, K. M., Rittenhouse, H. G., Millar, L. S., and Mikolajczyk, S. D. Benign prostatic hyperplasia-associated prostate-specific antigen (BPSA) shows unique immunoreactivity with anti-PSA monoclonal antibodies. Eur.J.Biochem., 267: 4040-4045, 2000.
25. Catalona, W. J., Partin, A. W., Slawin, K. M., Brawer, M. K., Flanigan, R. C., Patel, A., Richie, J. P., deKernion, J. B., Walsh, P. C., Scardino, P. T., Lange, P. H., Subong, E. N., Parson, R. E., Gasior, G. H., Loveland, K. G., and Southwick, P. C. Use of the percentage of free prostate-specific antigen to enhance differentiation of prostate cancer from benign prostatic disease: a prospective multicenter clinical trial. Jama, 279: 1542-1547, 1998.
26. Naughton, C. K., Smith, D. S., Humphrey, P. A., Catalona, W. J., and Keetch, D. W. Clinical and pathologic tumor characteristics of prostate cancer as a function of the number of biopsy cores: a retrospective study. Urology, 52: 808-813, 1998.
27. Lovgren, J., Rajakoski, K., Karp, M., Lundwall, A., and Lilja, H. Activation of the zymogen form of prostate-specific antigen by human glandular kallikrein 2. Biochem.Biophys.Res.Comm., 238: 549-555, 1997.
28. Takayama, T. K., Fujikawa, K., and Davie, E. W. Characterization of the precursor of prostate-specific antigen-activation by trypsin and by human glandular kallikrein. J.Biol.Chem., 272: 21582-21588, 1997.
29. Darson, M. F., Parcelli, A., Roche, P., Rittenhouse, H. G., Wolfert, R. L., Young, C. Y. F., Klee, G. G., Tindall, D. J., and Bostwick, D. G. Human Glandular Kallikrein 2 (hK2) expression in prostatic intraepithelial neoplasia and adenocarcinoma: a novel prostate cancer marker. Urology, 49(6): 857-862, 1997.
30. Mikolajczyk, S. D., Millar, L. S., Wang, T. J., Rittenhouse, H. G., Marks, L. S., Song, W., Wheeler, T. M., and Slawin, K. M. A precursor form of prostate-specific antigen is more highly elevated in prostate cancer compared with benign transition zone prostate tissue. Cancer Res, 60: 756-759, 2000.
31. Catalona, W. J. Clinical utility of measurements of free and total prostate-specific antigen (PSA): a review. Prostate, Supplement 7: 64-69, 1996.
32. Linnet K. Necessary sample size for method comparison studies based on regression analysis. Clin Chem 1999;45: 882-94.
33. Linnet K. Evaluation of regression procedures for methods comparison studies. Clin Chem 1993;39:424-32.
34. Bland J M, Altman D G. Statistical methods for assessing agreement between two methods of clinical measurement. Lancet 1986;i:307-10.
35. Reid M C, Lachs M S, Feinstein A R. Use of methodologic standards in diagnostic test research. Getting better but still not good. JAMA 1995;274:645-51.
36. Krouwer J S. Cumulative distribution analysis graphs—an alternative to ROC curves [Tech Brief]. Clin Chem 1987;33:2305-6.
37. Albert A. On the use and computation of likelihood ratios in clinical chemistry. Clin Chem 1982;28:1113-9.
38. Solberg H E. Discriminant analysis. Crit Rev Clin Lab Sci 1978;9:209-42.
39. Matthews J N S, Altman D G, Campbell M J, Royston P. Analysis of serial measurements in medical research. Br Med J 1990;300:230-5.

We claim:

1. A diagnostic method for determining the presence of prostate cancer in a subject comprising the steps of:
   (a) contacting a PSA containing sample from the subject with an antibody or antigen binding fragment thereof selective for [−2]pPSA, wherein the PSA containing sample is selected from the group consisting of prostate tissue, prostate cells from prostate tissue, blood, serum, plasma, seminal fluid, and urine;
   (b) determining the amount of [−2]pPSA contained in the PSA containing sample;
   (c) correlating the amount of the [−2]pPSA contained in the PSA containing sample to the presence of prostate cancer in the subject, wherein step (c) further comprises the steps of:
      (i) contacting the PSA containing sample with an antibody or antigen binding fragment thereof selective for free PSA;
      (ii) determining the amount of free PSA contained in the PSA containing sample;
      (iii) comparing the amount of [−2]pPSA to the amount of free PSA to generate a ratio for determining the presence of prostate cancer,
   wherein a value of the ratio comprising the amount of [−2]pPSA over the amount of free PSA of the subject greater than a cut-off value of the ratio comprising the amount of [−2]pPSA over the amount of free PSA is an indication of prostate cancer in the subject.

2. The method of claim 1 wherein step (a) comprises:
   (a) (i) contacting the PSA containing sample with the antibody or antigen binding fragment thereof under conditions that allow the formation of a binary complex comprising the antibody or antigen binding fragment thereof and the [−2]pPSA if present in the sample, and;
   (a) (ii) determining the amount of the complex.

3. The method of claim 1 wherein the antibody selective for [−2]pPSA is a monoclonal antibody.

4. The method of claim 2, wherein the complex is detected by a second antibody or antigen binding fragment thereof which comprises a detectable label or which is capable of binding to a detectable label for forming a detectable complex.

5. The method of claim 1 wherein the antibody selective for free PSA is a monoclonal antibody.

6. The method of claim 1, wherein the diagnostic method comprises densitometric analysis of [−2]pPSA and free PSA bands on a western blot, and the cut-off value of the ratio comprising [−2]pPSA over free PSA is about 0.25.

7. A diagnostic method for determining the presence of prostate cancer in a subject comprising the steps of:
   (a) contacting a PSA containing sample from the subject with an antibody or antigen binding fragment thereof selective for [−2]pPSA, wherein the PSA containing sample is selected from the group consisting of prostate tissue, prostate cells derived from prostate tissue, blood, serum, plasma, seminal fluid, and urine;

(b) determining the amount of [−2]pPSA contained in the PSA containing sample;

(c) correlating the amount of the [−2]pPSA contained in the PSA containing sample to the presence of prostate cancer in the subject, wherein step (c) further comprises the steps of:

(i) contacting the PSA containing sample with an antibody or antigen binding fragment thereof selective for free PSA;

(ii) determining the amount of free PSA contained in the PSA containing sample;

(iii) comparing the amount of free PSA to the amount of [−2]pPSA to generate a ratio for determining the presence of prostate cancer, wherein a value of the ratio comprising the amount of free PSA over the amount of [−2]pPSA of the subject less than a cut-off value of the ratio comprising the amount of free PSA over the amount of [−2]pPSA is an indication of prostate cancer in the subject.

8. The method of claim 7 wherein step (a) comprises:

(a) (i) contacting the PSA containing sample with the antibody or antigen binding fragment thereof under conditions that allow the formation of a binary complex comprising the antibody or antigen binding fragment thereof and the [−2]pPSA if present in the sample, and;

(a) (ii) determining the amount of the complex.

9. The method of claim 7 wherein the antibody selective for [−2]pPSA is a monoclonal antibody.

10. The method of claim 8, wherein the complex is detected by a second antibody or antigen binding fragment thereof which comprises a detectable label or which is capable of binding to a detectable label for forming a detectable complex.

11. The method of claim 7 wherein the antibody selective for free PSA is a monoclonal antibody.

12. The method of claim 7, wherein the diagnostic method comprises densitometric analysis of [−2]pPSA and free PSA bands on a western blot, and the cut-off value of the ratio comprising free PSA over [−2]pPSA is about 4.

* * * * *